(12) United States Patent
Hillukka et al.

(10) Patent No.: US 12,226,150 B2
(45) Date of Patent: Feb. 18, 2025

(54) ABLATION CATHETER TIP WITH FLEXIBLE ELECTRONIC CIRCUITRY

(71) Applicant: St. Jude Medical, Cardiology Division, Inc., St. Paul, MN (US)

(72) Inventors: Brett A. Hillukka, Hanover, MN (US); Andrew P. Wloch, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 709 days.

(21) Appl. No.: 17/442,882

(22) PCT Filed: Mar. 25, 2020

(86) PCT No.: PCT/IB2020/052831
§ 371 (c)(1),
(2) Date: Sep. 24, 2021

(87) PCT Pub. No.: WO2020/194214
PCT Pub. Date: Oct. 1, 2020

(65) Prior Publication Data
US 2022/0151691 A1    May 19, 2022

Related U.S. Application Data

(60) Provisional application No. 62/824,840, filed on Mar. 27, 2019.

(51) Int. Cl.
*A61B 18/14* (2006.01)
*A61B 18/00* (2006.01)
(Continued)

(52) U.S. Cl.
CPC .......... *A61B 18/1492* (2013.01); *H05K 1/118* (2013.01); *A61B 2018/00648* (2013.01);
(Continued)

(58) Field of Classification Search
CPC ...... A61B 18/1492; A61B 2018/00648; A61B 2018/00678; A61B 2018/00714;
(Continued)

(56) References Cited

U.S. PATENT DOCUMENTS 8,567,265 B2    10/2013  Aeby et al.
2015/0133914 A1  5/2015  Koblish
(Continued)

FOREIGN PATENT DOCUMENTS

EP     2742891 A1    6/2014
EP     2949282 A1   12/2015
(Continued)

OTHER PUBLICATIONS

European Search Report and Opinion in corresponding EP Patent Application No. 23184958.9, mailed Sep. 25, 2023, 8 pages.

*Primary Examiner* — Linda C Dvorak
*Assistant Examiner* — Abigail Bock
(74) *Attorney, Agent, or Firm* — Armstrong Teasdale LLP

(57) ABSTRACT

Aspects of the present disclosure are directed to, for example, a high-thermal-sensitivity ablation catheter tip including a thermally-insulative ablation tip insert supporting at least one temperature sensor electrically coupled to a flexible electronic circuit and encapsulated, or essentially encapsulated, by a conductive shell.

16 Claims, 21 Drawing Sheets

(51) Int. Cl.
  *H05K 1/11* (2006.01)
  *H05K 3/36* (2006.01)
(52) U.S. Cl.
  CPC ............... *A61B 2018/00678* (2013.01); *A61B 2018/00714* (2013.01); *A61B 2018/00797* (2013.01); *A61B 2018/00839* (2013.01); *A61B 2218/002* (2013.01); *H05K 3/363* (2013.01); *H05K 2201/053* (2013.01)
(58) Field of Classification Search
  CPC .......... A61B 2018/00797; A61B 2018/00839; A61B 2218/002; H05K 1/118; H05K 3/363; H05K 2201/053
  See application file for complete search history.

(56) References Cited

U.S. PATENT DOCUMENTS

| | | |
|---|---|---|
| 2016/0045133 A1 | 2/2016 | Balachandran et al. |
| 2016/0287312 A1 | 10/2016 | Tegg et al. |
| 2016/0287326 A1 | 10/2016 | Tegg et al. |
| 2016/0331471 A1 | 11/2016 | Deno et al. |
| 2017/0042449 A1 | 2/2017 | Deno et al. |
| 2017/0049348 A1 | 2/2017 | Deno et al. |
| 2018/0092688 A1* | 4/2018 | Tegg .................. A61B 18/1492 |
| 2018/0092689 A1 | 4/2018 | Tegg et al. |
| 2020/0038100 A1 | 2/2020 | Hillukka et al. |
| 2021/0022803 A1 | 1/2021 | Olson et al. |

FOREIGN PATENT DOCUMENTS

| | | |
|---|---|---|
| EP | 3020355 A1 | 5/2016 |
| EP | 3023070 A1 | 5/2016 |
| EP | 3292833 A1 | 3/2018 |
| EP | 3892222 A1 | 10/2021 |
| WO | 9308755 A1 | 5/1993 |
| WO | 2015065966 A2 | 5/2015 |
| WO | 2017087740 A1 | 5/2017 |

* cited by examiner

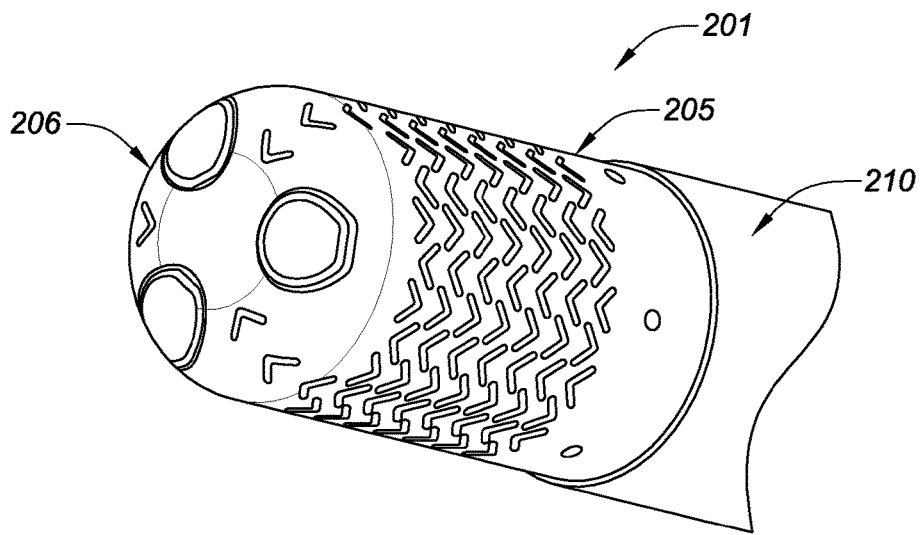
FIG. 2A
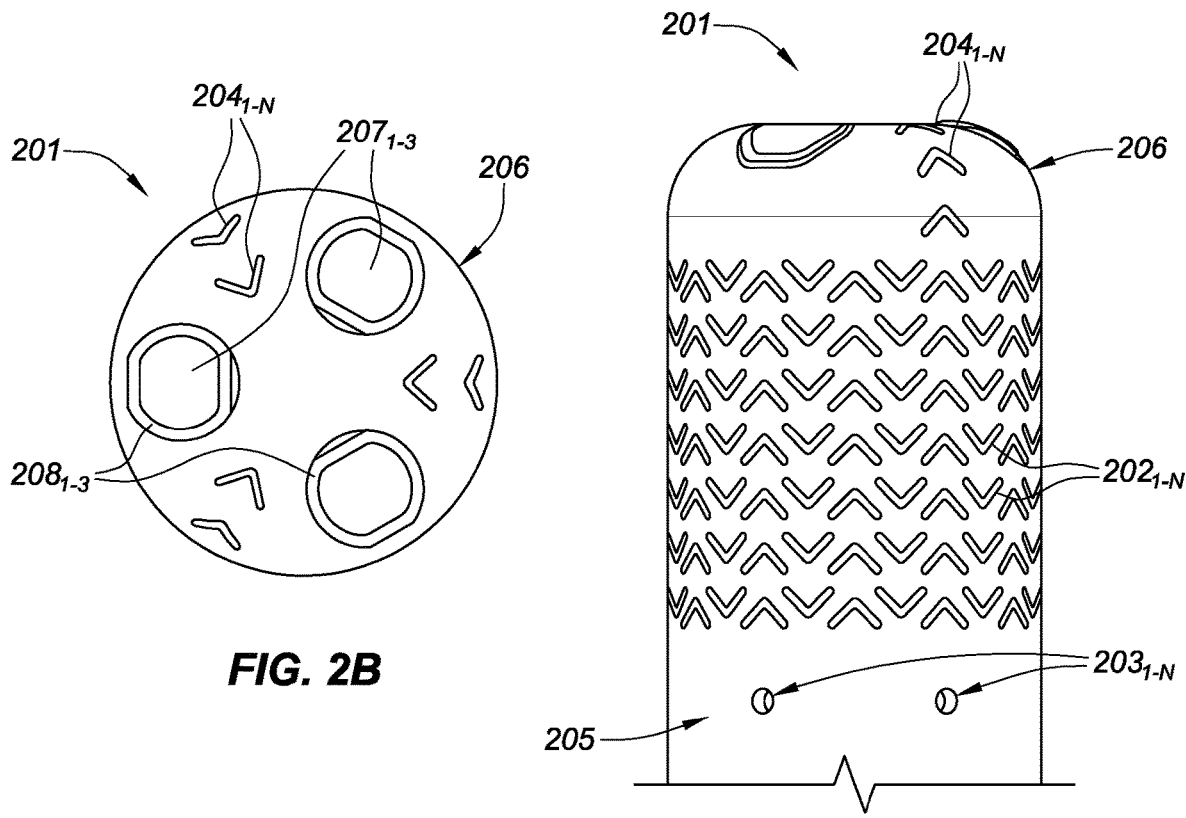
FIG. 2B
FIG. 2C

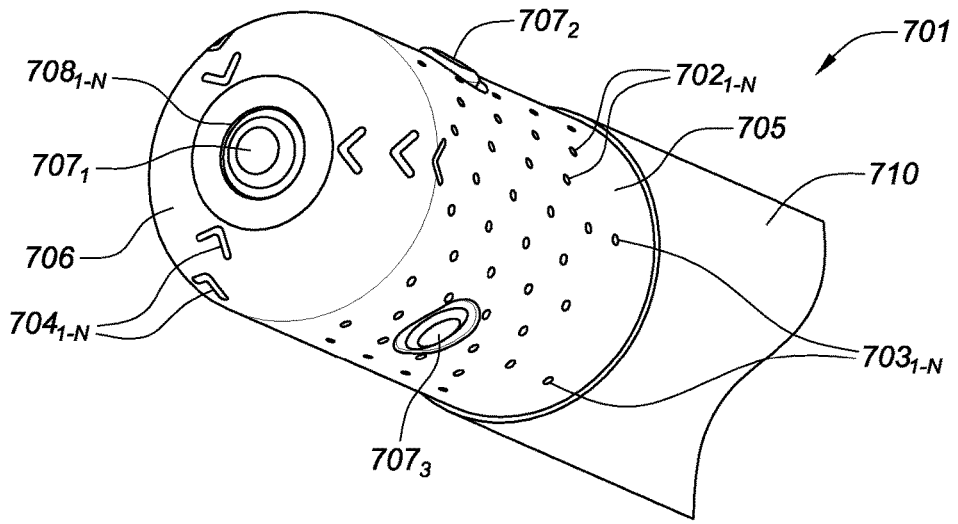
FIG. 7B
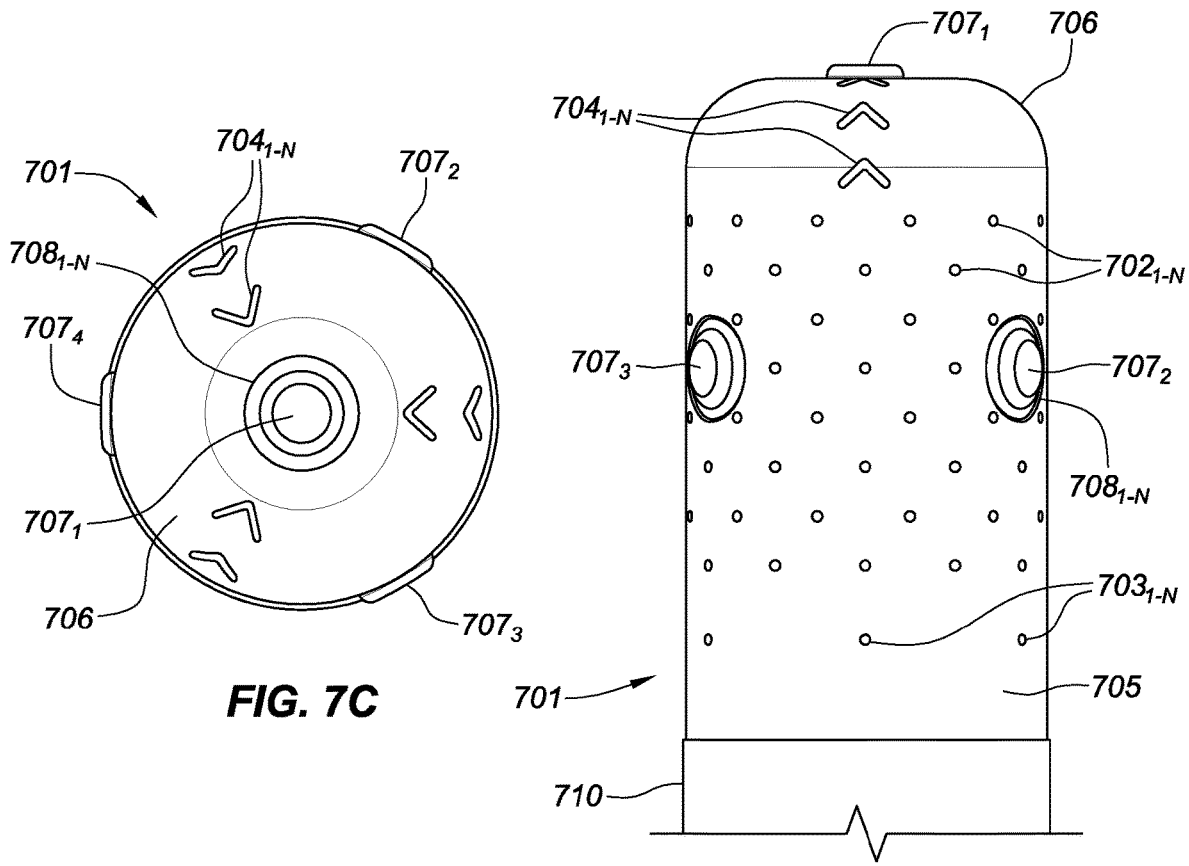
FIG. 7C
FIG. 7A

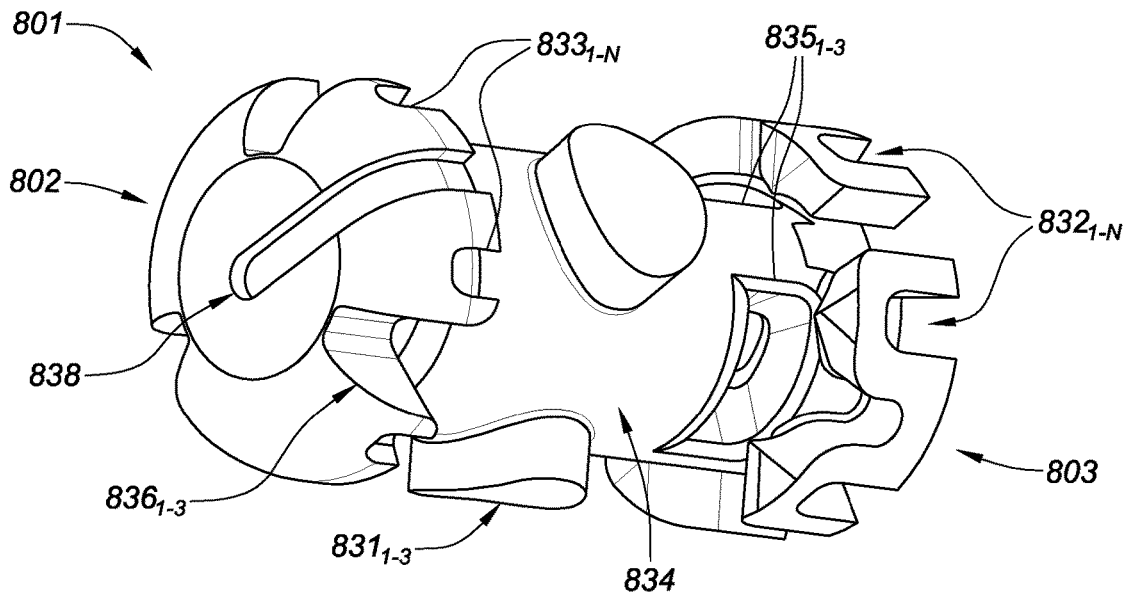
FIG. 8A
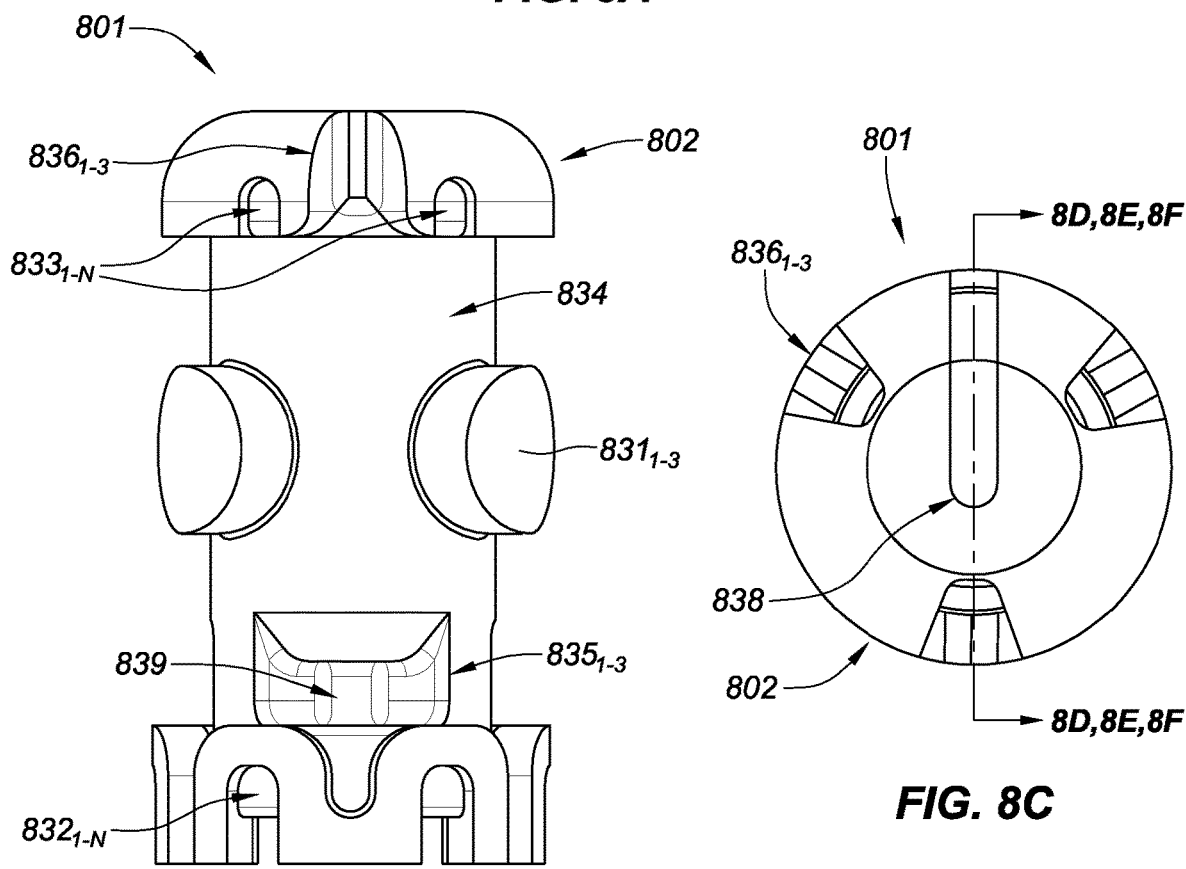
FIG. 8B
FIG. 8C

ABLATION CATHETER TIP WITH FLEXIBLE ELECTRONIC CIRCUITRY

CROSS-REFERENCE TO RELATED APPLICATIONS

This application is a national stage filing of PCT/IB2020/052831, filed 25 Mar. 2020, which claims the benefit of U.S. provisional application No. 62/824,840, filed 27 Mar. 2019, the disclosures of which are hereby incorporated by reference as though fully set forth herein.

This application incorporates by reference as though fully set forth herein, U.S. application Ser. No. 15/088,036, filed 31 Mar. 2016, now pending, which claims the benefit of U.S. provisional application No. 62/141,066, filed 31 Mar. 2015; U.S. application Ser. No. 15/088,052, filed 31 Mar. 2016, now pending, which claims the benefit of U.S. provisional application No. 62/198,114, filed 28 Jul. 2015; U.S. application Ser. No. 15/723,701, filed 3 Oct. 2017, now pending, which claims the benefit of U.S. provisional application No. 62/404,038, filed 4 Oct. 2016; international application no. PCT/US2017/049264, filed 30 Aug. 2017, now pending, which claims the benefit of U.S. provisional application No. 62/404,013, filed 4 Oct. 2016; and U.S. application Ser. No. 15/724,157, filed 3 Oct. 2017, now pending, which claims the benefit of U.S. provisional application No. 62/404,060, filed 4 Oct. 2016. This application is related to U.S. provisional application No. 62/824,844, filed 27 Mar. 2019, and U.S. provisional application No. 62/824,846 filed 27 Mar. 2019, both of which are incorporated by reference as though fully set forth herein.

BACKGROUND OF THE DISCLOSURE

The present disclosure relates to low thermal mass ablation catheter tips (also known as high-thermal-sensitivity catheter tips) and to systems for controlling the delivery of ablation energy to such catheter tips during tissue ablation therapy.

The foregoing discussion is intended only to illustrate the present field and should not be taken as a disavowal of claim scope.

BRIEF SUMMARY OF THE DISCLOSURE

Aspects of the present disclosure are directed to precise control of ablation energy delivery to a catheter to facilitate the formation of adequate lesions in tissue, while mitigating against tissue overheating. Accordingly, an ablation catheter tip may include high thermal sensitivity materials and a plurality of thermocouples in thermal communication therewith which facilitate near real-time (regional) temperature sensing at the ablation catheter tip. In some specific implementations, the plurality of thermocouples may be coupled to a flexible electronic circuit which also facilitates communication of the thermocouple signals to controller circuitry.

One embodiment of the present disclosure is directed to a a high-thermal-sensitivity ablation catheter tip. The tip including a conductive shell, a thermally-insulative tip insert, a flexible electronic circuit, plurality of thermal sensors and a plurality of microelectrodes. The conductive shell conducts ablation therapy. The thermally-insulative tip insert is positioned so that the conductive shell surrounds at least a portion of the tip insert. The flexible electronic circuit extends around the tip insert. The plurality of thermal sensors are placed in thermal communication with the conductive shell, and are distributed across at least one of a length and width of the flexible electronic circuit. The plurality of microelectrodes are electrically insulated from the conductive shell and sense electrophysiology characteristics of contacted tissue. The plurality of microelectrodes are coupled to a distal face of the tip insert and extend through the conductive shell. In more specific embodiments, the flexible electronic circuit includes a wired or wireless communication pathway at least partially disposed on the flexible electronic circuit. The wired or wireless communication pathway is communicatively coupled to the plurality of thermal sensors and the plurality of microelectrodes, and reports directional temperature feedback and data indicative of the electrophysiology characteristics of the contacted tissue to an ablation control system.

Another embodiment of the present disclosure is directed to an ablation tip for an ablation catheter. The ablation tip includes a thermally and electrically conductive shell that includes an inner surface, a thermally-insulative tip insert, and a flexible electronic circuit. At least a portion of the thermally-insulative tip insert is surrounded by the conductive shell. The flexible electronic circuit is circumferentially mounted around the tip insert and between the conductive shell and the thermally-insulative tip insert. The flexible electronic circuit includes one or more microelectrodes electrically insulated from the conductive shell. The one or more microelectrodes sense electrophysiology characteristics of contacted tissue, and are coupled to a distal face of the tip insert and extend at least partially through the conductive shell. In more specific embodiments, the flexible electronic circuit further includes a plurality of thermal sensors in thermally-transmissive contact with the inner surface of the conductive shell. The plurality of thermal sensors sensing regional temperatures of the conductive shell.

In a third embodiment of the present disclosure, an ablation catheter tip having high-thermal-sensitivity is disclosed including a thermally-insulative ablation tip insert and a conductive shell. The thermally-insulative ablation tip insert supports at least one flexible electronic circuit including a plurality of temperature sensors and a plurality of microelectrodes communicatively and mechanically coupled thereto. The conductive shell fits around at least a portion of the insert and is in thermal-communication with the plurality of temperature sensors.

In a fourth embodiment of the present disclosure, an ablation catheter tip is disclosed including a conductive shell and a plurality of microelectrodes. The conductive shell includes a distal tip surface, a tubular portion, and a crown extending therebetween. The plurality of microelectrodes extend through apertures in the crown. In more specific embodiments, the ablation catheter tip further includes a flexible electronic circuit communicatively coupled to the plurality of microelectrodes, and a thermally-insulative ablation tip insert. The flexible electronic circuit is wrapped around at least a portion of a circumference of the tip insert. The plurality of microelectrodes are mounted on a distal surface of the ablation tip insert, and a sensing surface of each of the plurality of microelectrodes are flush with the crown of the conductive shell.

The foregoing and other aspects, features, details, utilities, and advantages of the present disclosure will be apparent from reading the following description and claims, and from reviewing the accompanying drawings.

DESCRIPTION OF THE DRAWINGS

Various example embodiments may be more completely understood in consideration of the following detailed description in connection with the accompanying drawings, in which:

FIG. 2A is an isometric side view of a distal tip portion of an ablation catheter, consistent with various aspects of the present disclosure.

FIG. 2B is a top view of the distal tip portion of FIG. 2A, consistent with various aspects of the present disclosure.

FIG. 2C is a side view of the distal tip portion of FIG. 2A, consistent with various aspects of the present disclosure.

FIG. 7A is a side view of a distal tip portion of an ablation catheter, consistent with various aspects of the present disclosure.

FIG. 7B is a isometric top view of the distal tip portion of FIG. 7A, consistent with various aspects of the present disclosure.

FIG. 7C is a top view of the distal tip portion of FIG. 7A, consistent with various aspects of the present disclosure.

FIG. 8A is an isometric side view of an insert for a distal tip portion of an ablation catheter, consistent with various aspects of the present disclosure.

FIG. 8B is a side view of the insert of FIG. 8A, consistent with various aspects of the present disclosure.

FIG. 8C is a top view of the insert of FIG. 8A, consistent with various aspects of the present disclosure.

FIG. 8D is a cross-sectional side view of a first embodiment of the insert of FIG. 8A, consistent with various aspects of the present disclosure.

FIG. 8E is a cross-sectional side view of a second embodiment of the insert of FIG. 8A, consistent with various aspects of the present disclosure.

Figure 1:
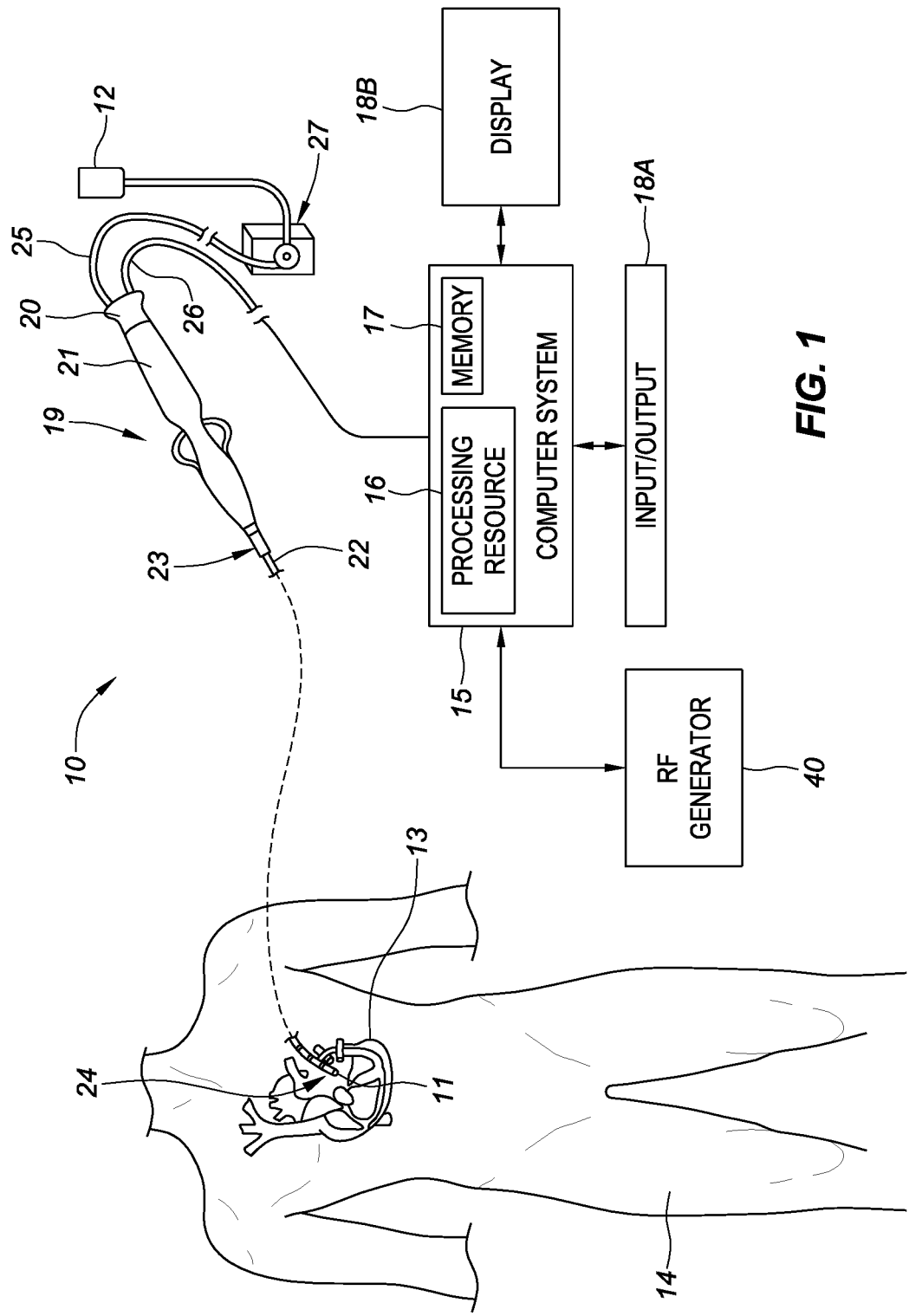
FIG. 1 is a diagrammatic overview of an ablation catheter system including a force sensing subsystem, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present disclosure are directed toward an ablation catheter tip including high thermal sensitivity ("HTS") materials and a plurality of thermocouples which facilitate near real-time (regional) temperature sensing at the ablation catheter tip. More specifically, aspects of the present disclosure are directed to a system for delivering ablation energy (e.g., pulsed radio-frequency ("RF") energy) to an ablation catheter during tissue ablation therapy. The ablation catheter may include a plurality of thermocouples to provide temperature feedback from the catheter to an ablation controller, which in turn varies the RF energy to the ablation catheter to effectively control tissue temperature during the ablation therapy. For example, the ablation controller may, rather than reducing the power to control temperature, provide power in a pulsed manner; and it is the control of the energy pulses, including control of the length of the time gaps between pulses, that facilitates ablation tip temperature control. The plurality of thermocouples may be positioned longitudinally and circumferentially about a distal tip of the ablation catheter to facilitate improved tissue temperature feedback accuracy and extrapolation of lesion depth and width.

To enable the ablation system, including temperature control as described above, to work most effectively, it may be desirable to mitigate thermal mass of a distal tip portion (or ablation tip). If the ablation tip has a relatively low thermal mass, it more rapidly heats (i.e., it comes to temperature quickly) and cools (i.e., it does not remain hot for long after power is removed), enabling tighter control of the tip temperature and less "coasting" of the tip temperature past a desired set point as well as more rapid reduction in tip temperature when power is removed from the tip. In fact, such a HTS ablation tip may cool down at the same rate as the tissue. This quick cool down is particularly useful to detect whether the tip is dislodged from the target tissue during ablation therapy.

In one embodiment of an ablation catheter system including an ablation catheter and a pulsed RF control system, the ablation catheter includes a conductive tip shell (e.g., a platinum shell, a platinum iridium shell, or a gold shell) with irrigation ports circumferentially distributed about the shell. As discussed in more detail below, the conductive shell may include irrigation ports in various configurations, patterns, and shapes (e.g., more or fewer holes, the size of the ports may be larger, or smaller, or a mix of larger and smaller holes, or the ports may include a combination of various shapes). In yet other embodiments, it may be unnecessary to irrigate the ablation catheter tip (e.g., the embodiment of FIGS. 1A-C do not include irrigation ports). Most of the discussion below focuses on irrigated catheter tip embodiments, but much of what is disclosed herein regarding irrigated catheter tip embodiments readily applies to the non-irrigated catheter tip embodiments disclosed.

A tip insert for the ablation catheter tip may be a unitary piece in some embodiments. The tip insert may be constructed from, for example, plastic (such as polyether ether ketone (PEEK), or polyetherimide ("ULTEM®")) or thermally-insulative ceramic. The tip insert may house six or more temperature sensors which may be radially disposed symmetrically about the catheter longitudinal axis. Various embodiments may include one or more rows longitudinally offset along the catheter longitudinal axis, and one or more temperature sensors may be positioned at/on a distal tip of the catheter. A central irrigation lumen delivers irrigant to irrigant ports in a distal tip shell and may be constructed from a polymer, such as polyimide. This central irrigation lumen may extend proximally toward a catheter handle, or may extend proximally all the way to the catheter handle. In some implementations the central irrigation lumen may be adhered directly to the tip insert.

The conductive tip shell may comprise a hemispherical or nearly-hemispherical domed distal end with a cylindrical body. The conductive tip shell may include a 'seam' between the domed distal end and the cylindrical body, which may be merely a circumferential transition line between the cylindrical body and the domed distal end of a unitary component; or, alternatively, it may be the location where the cylindrical body is coupled to the domed distal end. In one embodiment, the wall thickness of the shell is 0.002 inches, but various other alternative wall thicknesses are readily envisioned. The conductive tip shell may be formed or manufactured by, for example, forging, machining, drawing, spinning, or coining. Also, the conductive tip shell may be constructed from molded ceramic that has, for example, sputtered platinum on its external surface. In another alternative embodiment, the conductive tip shell may be constructed from conductive ceramic material.

An inner cylindrical surface of a conductive tip shell may be sized and configured to slide over a tip insert. In many embodiments, the tip insert positively positions a plurality of temperature sensors in close proximity (or more optimally direct contact) with the conductive tip shell. Where the conductive tip shell operates as an electrode for tissue ablation, the conductive tip shell is placed in good electrical contact with tip electrode lead wires. In some embodiments, the lead wires may be in-directly connected to the conductive tip shell via an intermediary part, such as a shank, in a manner that permits transfer of energy from the tip electrode lead wires to the shank and then to the conductive tip shell. Any voids in the assembled tip (other than the irrigation channels) may be filled with potting material, providing a durable ablation tip assembly. As discussed in brief above, it should also be noted that an outer surface of temperature sensors may be mounted in close proximity to, and preferably so as to be in physical contact with, an inner surface of the conductive shell. As used herein, "in close proximity to" means, for example, within 0.0002 to 0.0010 inches, particularly if a conductive adhesive or other bonding technique is used to bond the temperature sensors to the inner surface of the shell. Depending on the specific properties of the sensors, the construction and materials used for the shell, and the type of conductive adhesive or other bonding technique employed, it is possible that sufficient temperature sensitivity may be achieved despite the gaps between the sensors and the conductive shell, as long as the sensors are able to readily sense the temperature of tissue contacting an outer surface of the conductive tip shell during an ablation therapy.

Aspects of the present disclosure are directed to a conductive tip shell, instead of a solid platinum tip which is capable of absorbing much more thermal energy before a sensor embedded in the tip senses a temperature rise. Thus, in a solid platinum tip, not only does the portion of the tip in contact with the tissue being treated heat up, but also the entire tip gets hot, including portions of the tip that are remote from the tissue being treated. Moreover, blood flow around the entire solid platinum tip robs heat from the tip, further distorting the temperature sensed by the sensor embedded in the solid platinum tip (this may also limit the use of temperature averaging algorithms). For at least these reasons, the prior art solid platinum tip design is less capable of accurately reporting temperature in the immediate vicinity of the treated tissue. In contrast, in embodiments such as those depicted herein, a relatively thin conductive tip shell surrounding an insulative tip insert, the temperature of the conductive tip shell in the immediate vicinity of the tissue-tip interface heats up quickly, and the temperature sensor closest to that portion of the conductive tip shell rapidly senses and reports temperature rise due to the tissue-tip interface. It is not necessary for the entire ablation tip to heat up before the temperature sensor reports a temperature rise in the tissue. Further, the blood pool around the ablation tip has less of an opportunity to distort sensed tip temperature, and fewer temperature averaging issues result.

Experimental testing has determined that a number of advantages may be realized by positioning a temperature sensor as far distally on an ablation catheter tip as possible. For example, in view of the rapid heat dissipation experienced by these catheter tips, it can be extremely helpful to sense temperature at this distal location since it may be in the best location for accurately determining temperature of surrounding tissue during an ablation therapy. Accordingly, various embodiments of the present disclosure include at least one temperature sensor positioned as distal as possible on the catheter tip.

Further, it should be understood that, in other embodiments of a thermally-insulative ablation tip insert (both irrigated and non-irrigated embodiments), there may be more or fewer sensor mounting features. In fact, although the sensor mounting features may facilitate placement of the temperature sensors on the insert (e.g., during catheter assembly), the outer surface of the main body of the tip insert may be smooth. In such an embodiment, the sensors may be aligned with the smooth outer surface of the tip insert (and, possibly, held in place by, for example, adhesive). Then, when the conductive tip shell is placed around the tip insert, and the sensors are sandwiched between the outer surface of the tip insert and the inner surface of the conductive tip shell, the gaps (or voids) between the inner surface of the conductive shell and the outer surface of the tip insert may be filled with material (e.g., potting material or adhesive). It is worth noting that the sensors may be put in place before or after the conductive tip shell is placed over the tip insert. For instance, the sensors may be mounted on (e.g., adhered to) the smooth outer surface of the tip insert forming a tip-insert-sensor subassembly. Then, the conductive shell may be placed over that tip-insert-sensor subassembly before the remaining voids between the tip-insert-sensor subassembly and the conductive shell are filled. In some irrigated embodiments, the voids may be used as fluid irrigation channels to a plurality of irrigation ports extending through the conductive tip shell. Alternatively, the conductive tip shell may be held in place over the tip insert while one or more sensors are slid into the gap between the outer surface of the tip insert and the inner surface of the conductive shell. Subsequently, the voids could again be filled (or used as irrigant channels). These alternative manufacturing techniques apply to all of the disclosed embodiments that comprise sensors mounted between a tip insert and a conductive tip shell. In yet further embodiments disclosed herein, the plurality of temperature sensors may be mounted to one or more flexible electrical circuits and the one or more flexible electrical circuits may be circumferentially wrapped about the insert, with the one or more temperature sensors thereon placed into sensor mounting features in the tip insert.

In addition to ablation therapy, various embodiments of the present disclosure are directed to intravascular catheters capable of electrophysiology mapping. In such embodiments, a conductive shell includes cut-outs for one or more isolated electrophysiology electrodes ("EP electrodes"), which are insulated from the conductive shell which can act as an ablation electrode. In some embodiments, the EP electrodes may reside (partially) on the domed distal end of the conductive tip shell and/or (partially) on the cylindrical body of the conductive shell. In yet other embodiments, a plurality of EP electrodes may be positioned on a combination of the cylindrical body and domed distal tip, as described in more detail below. Each of these EP electrodes may be circumferentially encompassed by a strip of insulative material to reduce or eliminate any potential influence from the conductive tip shell.

While various embodiments of the present disclosure are directed to a conductive tip shell with a single-layer constructed from a thin layer of gold, for example, various embodiments may benefit from an outer layer including a paramagnetic material such as platinum or platinum iridium, for example. Such a paramagnetic material may improve magnetic resonance ("MR"). A multilayer conductive tip shell may have just a multilayer cylindrical body portion, just a multilayer domed distal end, or both a multilayer domed distal end and a multilayer cylindrical body. Again, however, it is not a requirement that the domed distal end and the cylindrical body must both be constructed with the same number of layers or with the same thickness of layers. Also, the walls of the conductive shell may, for example, be of a total thickness that is the same as, or nearly the same as, the thickness of the single-layer conductive tip shell described above. The conductive tip shell may be formed or manufactured per, for example, the techniques already described herein.

As mentioned above, an MR compatible catheter tip may comprise, for example, a single layer conductive shell constructed entirely from a diamagnetic material (e.g., gold) or a multilayer conductive shell. In one example of an MR compatible multilayer conductive shell, the conductive shell may comprise a platinum iridium outer layer (or skin) and an inner layer (or core) constructed from a diamagnetic material (e.g., gold or copper). In such an embodiment, the paramagnetic outer layer and the diamagnetic inner layer 'cooperate' in a manner that minimizes or mitigates against the generation of undesirable MR artifacts. In some multilayer embodiments (e.g., with a paramagnetic outer layer and a diamagnetic inner layer), it can be beneficial to mass balance or volume balance the material comprising the layers of the multilayer conductive shell. Alternatively, the multilayer conductive shell of the MR compatible catheter tip may have an outer layer constructed from a diamagnetic material (such as bismuth or gold) and an inner layer constructed from a paramagnetic material (such as platinum or platinum iridium).

In yet another embodiment, a multilayer conductive tip shell may comprise more than two layers. For example, the conductive tip shell may comprise three layers, including a very thin outer layer of a paramagnetic material, a thicker or intermediate layer of a diamagnetic material, and an oversized internal layer of a non-precious metal (or plastic or other material) sized to ensure that the finished geometry of the overall ablation tip is of a desired size for effective tissue ablation.

Materials that could be used for an inner layer or liner of a conductive tip shell include, but are not limited to, the following: silicon (metalloid); germanium (metalloid); bismuth (post transition metal); silver; and gold. Silver and gold are examples of elemental diamagnetic materials that have one-tenth the magnetic permeability of paramagnetic materials like platinum. Thus, one example multilayer shell configuration could comprise a platinum outer layer and an inner layer of gold or silver with a thickness ratio (e.g., platinum-to-gold thickness ratio) of at least $1/10$ (i.e., the platinum layer being one-tenth as thick as the gold layer). In another example embodiment, a multilayer conductive tip shell configuration may comprise a platinum outer layer and a bismuth inner layer with a thickness ratio (e.g., platinum-to-bismuth thickness ratio) of at least $1/2$ (i.e., the platinum outer layer being one-half as think as the bismuth inner layer) since bismuth has a permeability that is about one-half the permeability of platinum. The various layers may also be constructed from alloys, which may be used, for example, when a pure element material might otherwise be disqualified from use in the construction of the catheter tip.

Aspects of the present disclosure are directed to facilitating enhanced clinician understanding of an ablation therapy environment. A distal tip portion of the ablation catheter may include one or more rows of temperature sensors (circumferentially extending about the distal tip) which may be deployed along a length of the ablation tip. In one embodiment, a first row of temperature sensors may be positioned in close proximity to a distal tip of the catheter, and a second row spaced slightly more proximal to the first row. With more temperature sensors positioned about the ablation catheter tip, a higher-resolution 'picture' of the thermal tip profile and, therefore, a better understanding of tissue temperature near the catheter tip during ablation may be determined. This may be particularly beneficial when used in conjunction with a pulsed RF ablation control system (or a more typical temperature-controlled RF ablation control system).

Communicatively coupling a plurality of temperature sensors of the high thermal sensitivity ablation catheter tip with control circuitry may be facilitated by a (multi-layer) flexible circuit, consistent with various aspects of the present disclosure. In such embodiments, the flexible circuit may be installed on a tip insert of a catheter tip assembly instead of utilizing individually wired temperature sensors (and electrophysiology electrodes). By consolidating the various wire leads into one or more flexible circuits, or even one or more flexible circuits plus a few wire leads, the cost, complexity, and manufacturing assembly time associated with such ablation tip assemblies may be greatly reduced. In some specific implementations, lead wire count extending through a catheter shaft of a catheter ablation system may be reduced. Moreover, the flexible circuit may further include one or more electrical contacts for electrically coupling to spot electrodes. These electrodes, when capacitively coupled to tissue, may collect electrophysiology data related to the tissue (e.g., myocardial tissue). This electrophysiology data is then communicated through traces on the flexible circuit to controller circuitry. In yet other embodiments, microelectrodes may be used instead of spot electrodes on the flexible circuit, further reducing assembly complexity as the microelectrodes may be assembled onto the flexible circuit during production using, for example, surface mount technology placement equipment. In some embodiments, the thermal sensors and/or microelectrodes (and all associated circuitry, e.g., traces, vias, etc.) may be directly printed on a substrate of the flexible circuit.

To facilitate coupling of a flexible circuit to a tip insert or other structure, apertures may extend through the flexible circuit board. In such embodiments, a protrusion may extend out from an external surface of a tip insert, and extend through mating apertures in the flexible circuit board. Once properly located, the protrusions may be heat staked to create an interference fit between the apertures and the protrusion to permanently couple them. In the alternative, the flexible circuit board may include bonding locations that facilitate such coupling. It is to be understood that various coupling means may be utilized, including: ultrasonic welding, fasteners, adhesives, friction and compression fits, etc. to achieve coupling of the flexible circuit board to the tip insert. In yet further embodiments, to facilitate thermal coupling between temperature sensors and an inner surface of a conductive tip shell, the thermocouples may be directly coupled to the conductive tip shell; thereby obviating any precise fitting required between the thermocouples and the conductive shell. In various embodiments consistent with the present disclosure, a quick thermal response of the thermocouples is desirable to provide an ablation control system with low lag control inputs. Absent quick thermal response, over ablation of tissue may result.

It is to be understood that various circuit board layouts may be utilized to facilitate application specific design constraints of the flexible circuit board, consistent with the present disclosure. For example, to limit circuit board area, additional PCB layers may be added where the Z-dimension of a given application allows. Similarly, more or less connectors may be implemented. In yet further embodiments, wireless communication circuitry and/or a power supply may be embedded on the flexible circuitry to alleviate the need for electrical connections running the length of the catheter shaft altogether.

In the various embodiments disclosed herein, a flexible circuit board within the distal tip of the ablation catheter may include three layers: a copper layer at a top surface, an intermediate polyimide layer, and a constantan layer opposite the cooper layer. Each of the thermocouples may be formed by drilling a via through the copper, polyimide, and constantan layers, and through plating the via with copper. Either side of the thermocouple is then electrically coupled to a trace on its respective layer. Various thermocouple designs may also utilize an outer polyimide layer on both sides of the flexible circuit board to electrically insulate the thermocouples from irrigant. Various thermocouple design and manufacturing methods are well known in the art. The voltage across the two traces may be compared, and the resulting voltage change is indicative of a temperature of a conductive shell thermally coupled to the thermocouple. In various applications, including ablation therapies, as the conductive shell is in direct contact with tissue being ablated, efficacy of an ablation therapy may be surmised.

In many of the present embodiments, the flexible circuit in the ablation catheter distal tip is designed to facilitate individual addressability of each of the plurality of thermocouples situated therein. In more simplified embodiments, the plurality of thermocouples may be electrically coupled in parallel to effectively facilitate temperature averaging of the thermocouples, and to minimize the size of the flexible circuit extending through the catheter shaft. Such an embodiment may be particularly useful in applications where determining a tissue contact point along a circumference of the ablation catheter is not necessary. The present embodiment may also limit the effect of minute hot zones on an ablation control system.

As is well known in the arts, thermocouples typically comprise two dissimilar metals joined together at respective ends of the dissimilar metals. An end of the thermocouple placed into thermal contact with a hot object is called the hot junction, while the opposite end, which is disposed to a base-line temperature within the tip insert, is a cold junction. The hot junction in the top copper layer and the cold junction in the constantan layer are electrically coupled to one another through the polyimide layer. When a catheter tip, consistent with the present embodiment, is placed against a warm object, such as myocardial tissue being ablated by pulsed radio frequencies, a voltage difference across the hot and cold junctions develop. The voltage difference is correlated with a temperature of the hot junction. The materials of the hot and cold junctions may include one or more of the following materials: iron, nickel, copper, chromium, aluminum, platinum, rhodium, alloys of any of the above, and other metals with high conductivity.

To conduct electrophysiology mapping of tissue in contact with the ablation catheter tip, electrical signals from each of the spot/micro electrodes on the distal tip are compared and analyzed to detect electrophysiological characteristics indicative of medical conditions, such as, atrial fibrillation. Similarly, during and after treatment, the electrodes may be used to conduct diagnostics and determine an efficacy of a treatment, for example the strength and directionality of electrical signals being transmitted through the tissue.

While various high thermal sensitivity ablation catheter embodiments are disclosed in more detail in reference to the figures, a number of advantages may be realized by positioning a temperature sensor as far distally on the catheter tip as possible. For example, in view of the rapid heat dissipation experienced by catheter tips, it can be extremely helpful to sense temperature at this distal location since it may be in the best location for accurately determining the temperature of surrounding tissue during certain procedures.

Where the catheter tip assembly includes a conductive tip shell which functions as the ablation electrode, to reduce RF-related interference to the signals received by the EP electrodes, it may be advantageous to electrically isolate the spot electrodes from the rest of conductive tip shell and an RF emitter within the catheter tip assembly (if any). Accordingly, various embodiments of the ablation catheter disclosed herein include electrically insulative material that at least partially circumscribes the electrodes to prevent/limit RF-related signal interference received by the electrodes.

As discussed in more detail below in relation to the various embodiments presented in the figures, temperature sensors may be positioned across the multi-layer flexible circuit which is then wrapped around a tip insert. The temperature sensors which are now distributed about a circumference and length of a distal portion of the ablation catheter facilitate detection of temperatures across a surface of a conductive tip shell which covers the flexible circuit and is in thermal communication therewith. The flexible circuit, during assembly of the ablation catheter, may be wrapped around a tip insert and sandwiched between the tip insert and the conductive tip shell.

Prior to the discoveries of the present disclosure, ablation catheters with electrophysiology monitoring capability required separate spot electrode components, increasing cost and complexity of the ablation catheters. Aspects of the present disclosure eliminate the need for additional components, reducing cost and simplifying the assembly of the tip. For example, various embodiments of the present disclosure include a catheter tip design which utilizes a flexible printed circuit with microelectrodes and temperature sensors thereon, and which carries electrical signals from the microelectrodes and the temperature sensors to a connector in the catheter handle. Moreover, because the microelectrodes are part of the flexible circuit, no additional components are required at the distal tip portion of the ablation catheter to facilitate their functionality.

Aspects of the present disclosure facilitate a clinician's ability to measure localized electrograms and impedance with the ablation catheter to improve patient outcomes during ablation therapies, and to remove the necessity for a second, electrophysiology catheter to be utilized. As will be discussed in more detail below in reference to FIGS. 1A-C, among other embodiments, a flexible circuit is coupled to an insert, the flexible circuit and the insert are then inserted into the tip shell before microelectrodes are placed thru through holes in the tip shell and communicatively coupled to the flexible circuit. In yet other embodiments, the flexible circuit including the microelectrodes may be coupled to an insert, and the microelectrodes extend thru through holes in the tip shell as the insert is assembled with the tip shell. The microelectrode may be flush with an outer surface of the tip shell, or positioned proud relative to the outer surface of the tip shell.

In the various embodiments of the flexible circuit board described herein, a substrate of the flex circuit may comprise polyimide, and a sensing surface of the microelectrodes may be copper, gold-plated, Pt/Ir plated, or plated/coated with another material that provides desirable electrogram and tissue impedance measuring capability, meet microbiology/biocompatibility requirements, and application-specific durability requirements (e.g., extreme heat tolerance associated with RF ablation). It is to be understood that the shape, size, placement, and number of microelectrodes may widely vary from the example embodiments described in more detail herein based on application specific requirements. Moreover, in various embodiments microelectrodes may also be substituted with hybrid-type electrode/temperature sensor elements. In such an embodiment, the outer layers of the flex circuit may contain microelectrodes and their respective traces, and the underlying layers may contain the thermocouples and their respective traces. This application incorporates by reference as though fully set forth herein international application no. PCT/US2018/046953, filed 17 Aug. 2018, now pending, which claims the benefit of U.S. provisional application No. 62/546,911, filed 17 Aug. 2017.

Aspects of the present disclosure are further directed to an ablation catheter which combines high thermal sensitivity with evenly distributed irrigant delivery capability. These embodiments solve the problem of having high thermal sensitivity in an ablation tip for safety, lesion prediction and closed loop ablation control, but not having evenly distributed irrigation across the tip. Prior art ablation catheters with more limited tip irrigation suffer from occurrences of char, coagulation, and steam pops during ablation. To solve such problems, aspects of the present disclosure utilize more evenly distributed irrigant port patterns across the tip. In some specific embodiments, a conductive tip shell comprises a platinum and iridium (Pt/Ir) composition with laser cut irrigant ports that allow for the desired distributed irrigation affect, and a thermally insulated tip insert that holds the thermocouples in precise positions about the ablation tip and in thermal contact with the tip shell. The tip insert further directs the internal irrigant flow to achieve even distribution circumferentially and longitudinally about the ablation tip. Moreover, the tip insert helps to insulate the temperature sensors from the irrigant.

Referring now to the drawings wherein like reference numerals are used to identify identical components in the various views, FIG. 1 generally illustrates an ablation catheter system 10 having an elongated medical device 19 that includes a sensor assembly 11 (e.g., fiber optic based distance measurement sensor) configured to be used in the body for medical procedures. The elongated medical device 19 may be used for diagnosis, visualization, and/or treatment of tissue 13 (such as cardiac or other tissue) in the body. For example, the medical device 19 may be used for ablation therapy of tissue 13 or mapping of a patient's body 14. FIG. 1 further illustrates various sub-systems included in the ablation catheter system 10. The system 10 may include a main computer system 15 (including an electronic control unit 16 and data storage 17, e.g., memory). The computer system 15 may further include conventional interface components, such as various user input/output mechanisms 18A and a display 18B, among other components. Information provided by the sensor assembly 11 may be processed by the computer system 15 and may provide data to the clinician via the input/output mechanisms 18A and/or the display 18B, or in other ways as described herein. Specifically, the display 18B may visually communicate a force exerted on the elongated medical device 19—where the force exerted on the elongated medical device 19 is detected in the form of a deformation of at least a portion of the elongated medical device by the sensor assembly 11, and the measured deformation is processed by the computer system 15 to determine the force exerted.

In the illustrative embodiment of FIG. 1, the elongated medical device 19 may include a cable connector or interface 20, a handle 21, a tubular body or shaft 22 having a proximal end 23 and a distal end 24. The elongated medical device 19 may also include other conventional components not illustrated herein, such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the elongated medical device 19.

The handle 21 provides a portion for a user to grasp or hold the elongated medical device 19 and may further provide a mechanism for steering or guiding the shaft 22 within the patient's body 14. For example, the handle 21 may include a mechanism configured to change the tension on a pull-wire extending through the elongated medical device 19 to the distal end 24 of the shaft 22 or some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the sensor assembly 11. For example, if contact to tissue 13 is made by distal end 24, the sensor assembly 11 may transmit data to the computer system 15 indicative of contact. In response to the computer system 15 determining that the data received from the sensor assembly 11 is indicative of contact between the distal end 24 and a patient's body 14, the computer system 15 may operate a light-emitting-diode on the handle 21, a tone generator, a vibrating mechanical transducer, and/or other indicator(s), the outputs of which could vary in proportion to the calculated contact force.

The computer system 15 may utilize software, hardware, firmware, and/or logic to perform a number of functions described herein. The computer system 15 may be a combination of hardware and instructions to share information. The hardware, for example may include processing resource 16 and/or a memory 17 (e.g., non-transitory computer-readable medium (CRM) database, etc.). A processing resource 16, as used herein, may include a number of processors capable of executing instructions stored by the memory resource 17. Processing resource 16 may be integrated in a single device or distributed across multiple devices. The instructions (e.g., computer-readable instructions (CRI)) may include instructions stored on the memory 17 and executable by the processing resource 16 for force detection.

The memory resource 17 is communicatively coupled with the processing resource 16. A memory 17, as used herein, may include a number of memory components capable of storing instructions that are executed by processing resource 16. Such a memory 17 may be a non-transitory computer readable storage medium, for example. The memory 17 may be integrated in a single device or distributed across multiple devices. Further, the memory 17 may be fully or partially integrated in the same device as the processing resource 16 or it may be separate but accessible to that device and the processing resource 16. Thus, it is noted that the computer system 15 may be implemented on a user device and/or a collection of user devices, on a mobile device and/or a collection of mobile devices, and/or on a combination of the user devices and the mobile devices.

The memory 17 may be communicatively coupled with the processing resource 16 via a communication link (e.g., path). The communication link may be local or remote to a computing device associated with the processing resource 16. Examples of a local communication link may include an electronic bus internal to a computing device where the memory 17 is one of a volatile, non-volatile, fixed, and/or removable storage medium in communication with the processing resource 16 via the electronic bus.

In various embodiments of the present disclosure, the computer system 15 may receive optical signals from a sensor assembly 11 via one or more optical fibers extending a length of the catheter shaft 22. A processing resource 16 of the computer system 15 may execute an algorithm stored in memory 17 to compute a force exerted on distal end 24, based on the received optical signals.

U.S. Pat. No. 8,567,265 discloses various optical force sensors for use in medical catheter applications, such optical force sensors are hereby incorporated by reference as though fully disclosed herein.

FIG. 1 further depicts an RF generator 40 operatively connected to the computer system 15, which is operatively connected to the elongated medical device 19. In this figure, a number of possible wired and/or wireless communication pathways are shown. For example, the computer system 15 may receive temperature feedback readings from at least one temperature sensor mounted on or near the distal end 24 of the catheter shaft 22. In various embodiments disclosed herein, the catheter may include multiple thermal sensors (for example, thermocouples or thermistors), as described further below. The temperature feedback readings may be the highest reading from among all of the individual temperature sensor readings, or it may be, for example, an average of all of the individual readings from all of the temperature sensors. The computer system 15 may then communicate to the RF generator 40 the highest temperature measured by any of the plurality of temperature sensors mounted within the sensor assembly 11. This could be used to trigger a temperature-based shutdown feature in the RF generator for patient safety. In other words, the temperature reading or readings from the catheter may be sent to the computer system 15, which may then feed the highest temperature reading to the RF generator 40 so that the generator can engage its safety features and shut down if the temperature reading exceeds a (safety) threshold.

While FIG. 1 is illustrated with an RF generator 40 for conducting tissue ablation at a distal end 24 of the catheter shaft 22, various other ablation energy sources may be readily utilized in the catheter system 10.

Figure 1A:
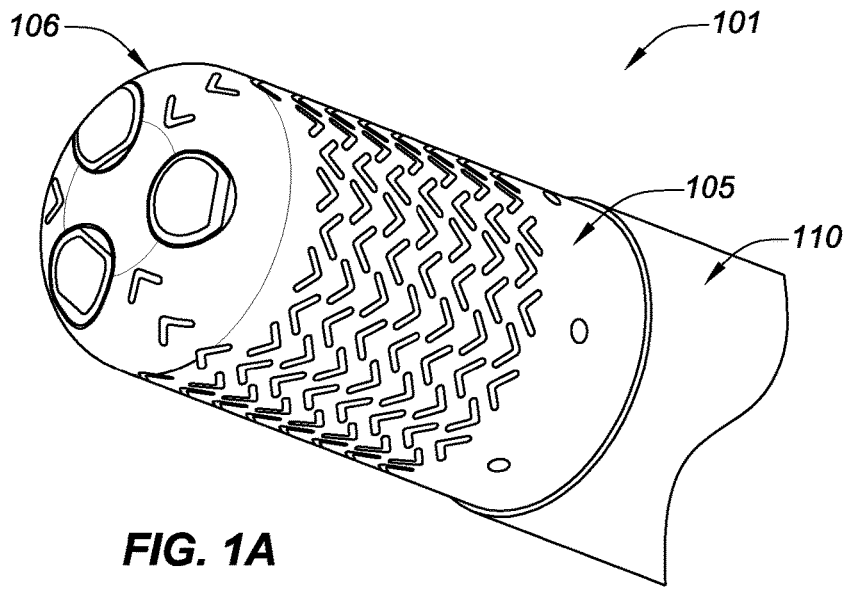
FIG. 1A is an isometric side view of a distal tip portion of an ablation catheter, consistent with various aspects of the present disclosure.
Figure 1B:
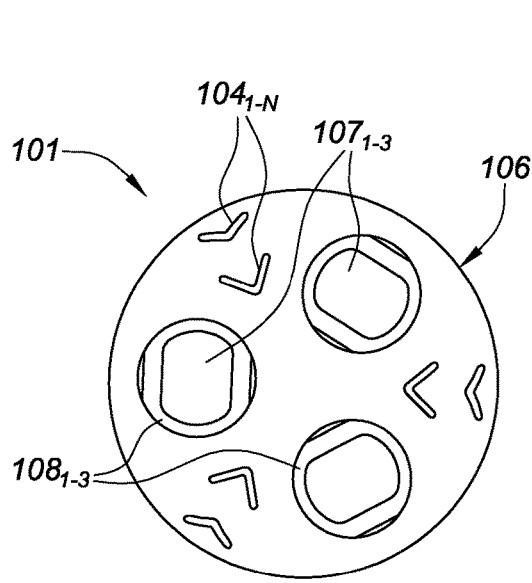
FIG. 1B is a top view of the distal tip portion of FIG. 1A, consistent with various aspects of the present disclosure.
Figure 1C:
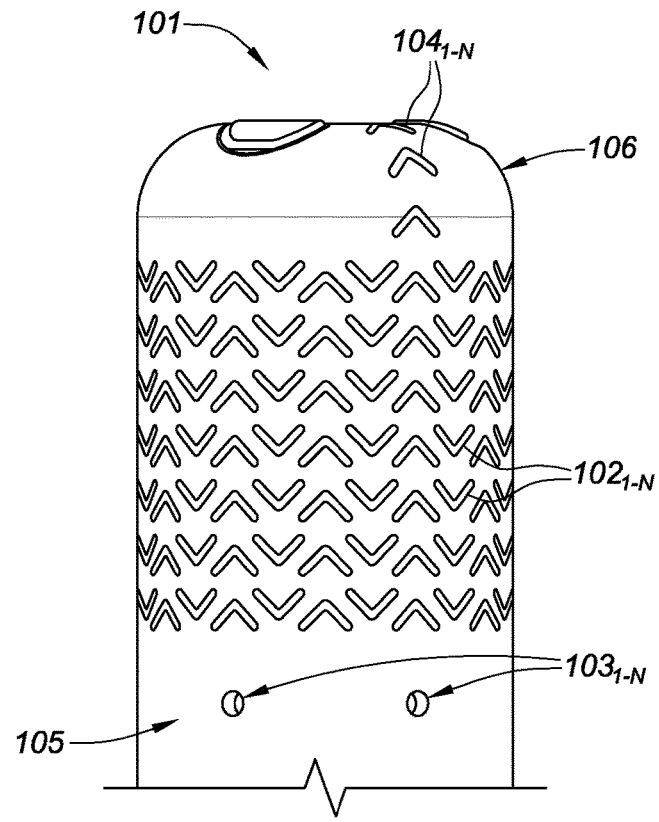
FIG. 1C is a side view of the distal tip portion of FIG. 1A, consistent with various aspects of the present disclosure.

FIG. 1A is an isometric side view of a distal tip portion 101 of an ablation catheter, FIG. 1B is a top view of the distal tip portion 101 of FIG. 1A, and FIG. 1C is a side view of the distal tip portion 101 of FIG. 1A, consistent with various aspects of the present disclosure. The distal tip portion 101 of the ablation catheter includes a conductive tip shell 105 which is coupled to a distal end of catheter shaft 110. In various embodiments of the present disclosure, the conductive tip shell may ablate myocardial tissue (or other tissue) using radio-frequency energy which is transmitted to the tissue via the conductive tip shell 105. To facilitate enhanced tissue contact, the conductive tip shell may be flexible and/or (partially) deformable. For example, as shown in FIGS. 1A-C, the conductive tip shell includes a plurality of chevron features $102_{1-N}$ which extend through the tip shell. In the present embodiment, the chevrons are aligned in distally and proximally facing columns which are interleaved with one another, and the rows of chevrons extend circumferentially about the conductive tip shell. The plurality of chevrons features $102_{1-N}$ function to facilitate delivery of irrigation fluid into proximity with the tissue. In some more specific embodiments, the plurality of chevrons features $102_{1-N}$ may also function to reduce the structural rigidity of the conductive tip shell 105 to maximize tissue contact.

As further shown in FIGS. 1A-C, one or more columns of the plurality of chevron features $102_{1-N}$ may extend distally onto a distal tip 106 of the conductive tip shell 105 to further facilitate enhanced irrigation at the distal tip portion. In the present embodiment, the chevron features $104_{1-N}$ at the distal tip 106 extend between electrophysiology electrodes $107_{1-3}$, which are circumferentially distributed about a longitudinal axis of the catheter shaft 110. The electrophysiology electrodes at the distal tip may facilitate electrophysiology analysis of tissue in contact with the distal tip before, during, and/or after an ablation therapy. To electrically insulate the electrophysiology electrodes $107_{1-3}$ from the conductive tip shell 105, an insulative layer $108_{1-3}$ circumferentially extends around the electrodes. In various embodiments, the electrophysiology electrodes $107_{1-3}$ are microelectrodes.

In the distal tip portion 101 of FIGS. 1A-C, a proximal portion of conductive tip shell 105 may or may not include additional irrigation apertures $103_{1-N}$. These additional irrigation apertures may be placed distal to a coupling between the conductive tip shell and the catheter shaft 110. In some embodiments, the additional irrigation apertures may not impact the structural integrity of the conductive tip shell, but instead merely function to irrigate the conductive tip shell 105. In the present embodiment, the additional irrigation apertures $103_{1-N}$ are circular apertures which are evenly distributed around a circumference of the distal tip portion 101. In some more specific embodiments, the additional irrigation apertures $103_{1-N}$ may be directed distally to help facilitate irrigation near the distal tip 106.

As will become apparent from the various embodiments disclosed in the present application, while many embodiments are presented with one or more types of irrigation features (e.g., chevron, aperture, nozzle, etc.), a skilled artisan will appreciate that various combinations and patterns of these irrigation features are readily envisioned.

To assemble the distal tip portion described in reference to FIGS. 1A-C, a flex circuit, containing thermocouples and microelectrodes, is wrapped around and secured to a tip insert. A sub-assembly (tip insert and flex circuit) is then inserted into the conductive tip shell 105 and secured in place. While the present embodiment includes microelectrodes oriented primarily towards the distal end of the ablation catheter, in many applications it may be desirable to have microelectrodes facing both distally and radially to achieve efficient electrogram and impedance data capture from the tissue regardless of tip-tissue orientation. A number of embodiments disclosed herein discuss such an embodiment. As another alternative, and discussed in more detail in reference to FIGS. 2A-2C, the distally-facing microelectrodes may be moved radially outward (e.g., positioned closer to a crown of the distal tip; the crown may otherwise be referred to as a round), causing the microelectrodes to face more radially than the embodiments disclosed in FIGS. 1A-C. This may be further facilitated by a curved sensing surface. Placement of the electrodes along the curved sensing surface facilitates the detection of electrophysiology characteristics of tissue in contact with not only a distal tip surface, but also the crown of the distal tip.

FIG. 2A is an isometric side view of a distal tip portion 201 of an ablation catheter, FIG. 2B is a top view of the distal tip portion 201 of FIG. 2A, and FIG. 2C is a side view of the distal tip portion 201 of FIG. 2A, consistent with various aspects of the present disclosure. The distal tip portion 201 is similar to distal tip portion 101 of FIGS. 1A-C, except that electrophysiology electrodes $207_{1-3}$ are further extended radially outwards. As a result, the electrophysiology electrodes are capable of making contact with tissue which may not be oriented perfectly perpendicular relative to a longitudinal axis of catheter shaft 210. FIG. 2C, in particular, shows the electrophysiology electrodes $207_{1-3}$ extending down along a radius of distal tip 206. As a result, when conductive tip shell 205 contacts tissue at a non-right angle, one or more of the electrodes may still make sufficient contact with the tissue to facilitate electrophysiology mapping or other electrical analysis. In yet other embodiments, disclosed in more detail below, additional electrophysiology electrodes may be added to a proximal portion of the conductive tip shell 205 to further facilitate electrophysiology analysis of tissue which is positioned parallel relative to a longitudinal axis of catheter shaft 210.

Figure 2D:
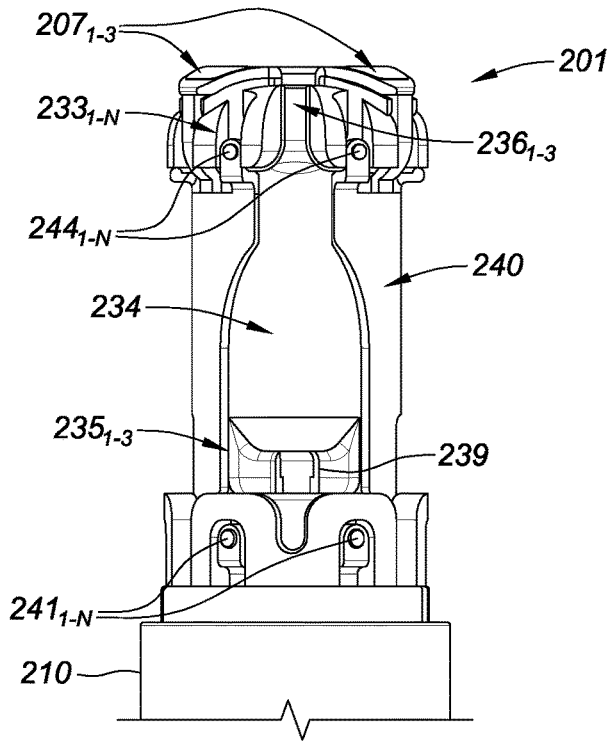
FIG. 2D is a partially assembled, side view of the distal tip portion of FIG. 2A, consistent with various aspects of the present disclosure.
Figure 2E:
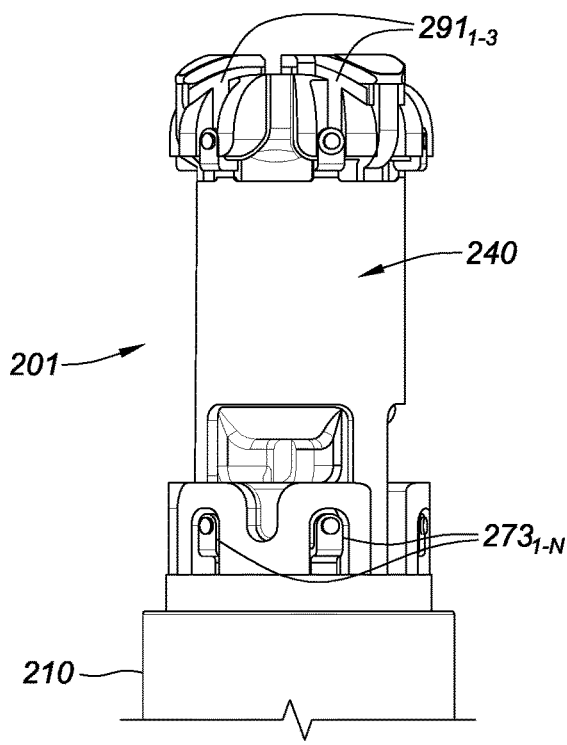
FIG. 2E is a partially assembled, front view of the distal tip portion of FIG. 2A, consistent with various aspects of the present disclosure.
Figure 2F:
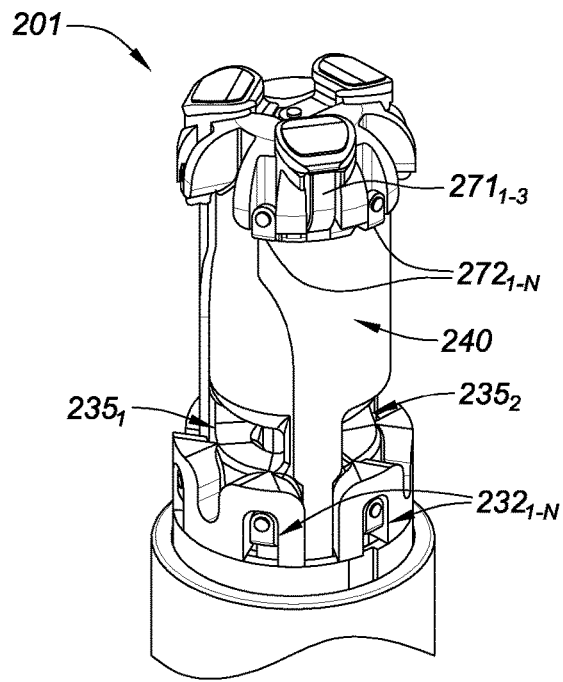
FIG. 2F is a partially assembled, isometric top view of the distal tip portion of FIG. 2A, consistent with various aspects of the present disclosure.
Figure 2G:
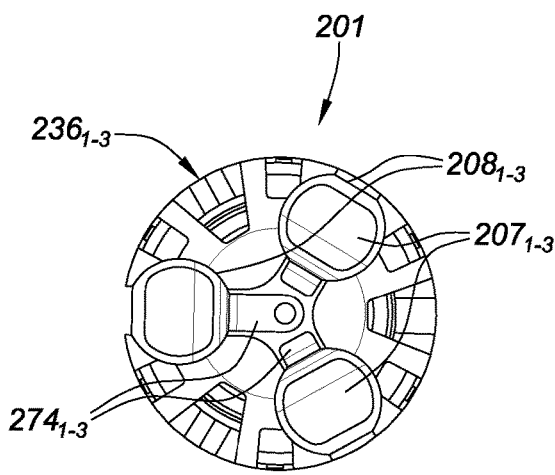
FIG. 2G is a partially assembled, top view of the distal tip portion of FIG. 2A, consistent with various aspects of the present disclosure.

FIG. 2D is a partially assembled, side view of the distal tip portion 201 of FIG. 2A, FIG. 2E is a partially assembled, front view of the distal tip portion 201 of FIG. 2A, FIG. 2F is a partially assembled, isometric top view of the distal tip portion 201 of FIG. 2A, and FIG. 2G is a partially assembled, top view of the distal tip portion 201 of FIG. 2A, consistent with various aspects of the present disclosure. As shown in FIGS. 2D-G, a tip insert 234 is coupled to a distal end of catheter shaft 210. A flexible electronic circuit 240 (or flex circuit) is coupled (circumferentially in some embodiments) to the tip insert. The flex circuit includes a plurality of temperature sensors which, in the present embodiment, are positioned in proximal and distal rings ($241_{1-N}$ and $244_{1-N}$, respectively) about the tip insert 234. The proximal and distal rings of temperature sensors facilitate high thermal sensitivity of the conductive tip shell (not shown). In the present embodiment, each of the temperature sensors, which are (communicatively) coupled to the flex circuit 240, extend out on flex circuit fingers ($272_{1-N}$ and $273_{1-N}$) and these fingers are mated to complimentary mounting features ($232_{1-N}$ and $233_{1-N}$) on the tip insert. In many embodiments, when a conductive tip shell is mated to the tip insert, the temperature sensors are sandwiched between the tip insert and tip shell; however, in some embodiments, the temperature sensors and/or flex circuit fingers may be further secured by adhesive or some other method well known in the art to the tip insert and/or tip shell. In yet further more specific embodiments, a conductive paste may be placed between the temperature sensors and the tip shell to further facilitate thermal transfer there between.

The use of flexible circuits with a plurality of temperature sensors communicatively coupled thereto reduces assembly complexity and cost for an ablation catheter with high thermal sensitivity.

While many of the present embodiments disclose a high thermal sensitivity ablation catheter with two rings of six temperature sensors each, various other configurations are readily envisioned. For example, more or less temperature sensors in each row, unevenly distributed temperature sensors in a particular ring, and one or more rings distributed along a length of the distal tip portion 201 of the ablation catheter. Moreover, in some embodiments, it may be desirable to place one or more temperature sensors on the distal tip of the ablation catheter (as shown in FIG. 2G, for example).

As discussed in more detail above, a distal tip portion 201 of the ablation catheter includes three electrophysiology electrodes $207_{1-3}$ on distal tip 206. The electrodes may be spot electrodes which are soldered to flex circuit 240 (in a secondary operation) or microelectrodes which are communicatively coupled to the flex circuit during manufacture of the flexible circuit using, for example, surface mount technology placement equipment. Similar to the temperature sensors, the electrodes may be positioned on a distal tip of the tip insert 234 via flex circuit fingers $271_{1-3}$ which extend from the flex circuit 240. The flex circuit fingers and thereby the electrophysiology electrodes may be secured to the distal tip of the insert via one or more securing mounts $274_{1-3}$ which are coupled to the tip insert via one or more known securing methods well known to a skilled artisan (e.g., adhesive). One or more of the flex circuit fingers $271_{1-3}$ may also include one or more traces for communicatively coupling one or more temperature sensors, positioned on the distal tip of the tip insert, to the rest of the flex circuit 240.

To facilitate precise positioning of the electrodes relative to a surface of, and openings in, the conductive tip shell, the electrodes may be placed on pedestals $291_{1-3}$.

Tip insert 234 further facilitates delivery of irrigant to the various irrigation ports in the conductive tip shell. In the present embodiment, catheter shaft 210 includes a central irrigation lumen 239 which extends from a catheter handle to a distal end of the catheter shaft. The irrigant enters a central lumen of the tip insert and is circumferentially distributed about the tip insert via three irrigation nozzles $235_{1-3}$. After exiting the irrigation nozzles $235_{1-3}$, the irrigant flows distally between the flex circuit 240 and an inner surface of a conductive tip shell before extending radially out of the plurality of irrigation ports (e.g., $202_{1-N}$ and $203_{1-N}$), and/or longitudinally out of distally facing irrigation ports $204_{1-N}$.

Figure 2H:
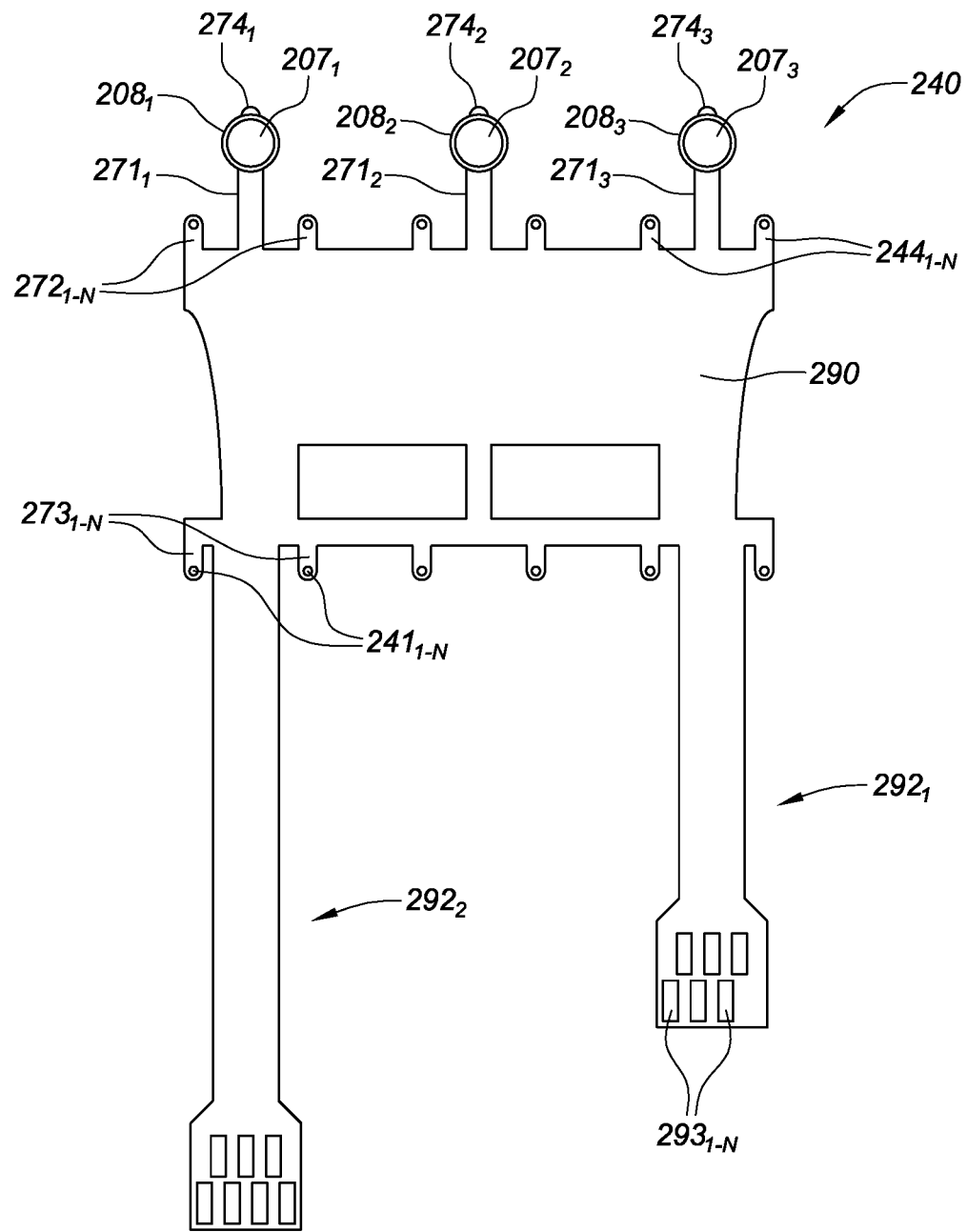
FIG. 2H is a top view of a flexible electronic circuit, consistent with various aspects of the present disclosure.

FIG. 2H is a top view of a flexible circuit 240, consistent with various aspects of the present disclosure. In various embodiments, the flexible circuit 240 may be installed on a tip insert of a catheter tip assembly instead of utilizing individually wired temperature sensors and electrophysiology electrodes. By consolidating the various wire leads into one or more flexible circuits, or even one or more flexible circuits plus a few wire leads, the cost, complexity, and manufacturing assembly time associated with such ablation tip assemblies may be greatly reduced.

Flexible circuit 240 may include one or more connectors 292 located at the distal end of a strand of the flexible circuit to facilitate manufacturability within a catheter tip sub-assembly. For example, where the catheter tip is completed in sub-assembly form prior to installation in a catheter shaft sub-assembly, the connectors 292 may extend from the catheter tip sub-assembly to facilitate coupling to another flexible circuit, or lead wires extending from the catheter shaft sub-assembly. To further facilitate assembly, the connectors 292 may be electrically coupled to the flexible circuit(s) of the catheter shaft sub-assembly via an electrical connector. Alternatively, solder pads of the two flexible circuits may be soldered to one another. The use of flexible circuits may also further facilitate automation of the catheter assembly process.

In FIG. 2H, electrical signals from distal and proximal thermocouple, $244_{1-N}$ and $241_{1-N}$, respectively, on flexible circuit board 290 may be isolated from one another by extending traces from the proximal thermocouples $241_{1-N}$ to solder pads $293_{1-N}$ on connector $292_1$, and traces from the distal thermocouples $244_{1-N}$ to solder pads $293_{1-N}$ on connector $292_2$. This example circuit board routing mitigates electrical and electromagnetic cross-talk (interference) between the un-shielded electrical traces. The various electrical traces on the flexible circuit board 290 form a communication pathway. The distal and proximal thermocouple, $244_{1-N}$ and $241_{1-N}$, respectively, on flexible circuit board 290 extend out from a body of the circuit board 290 via flex circuit fingers $272_{1-N}$ and $273_{1-N}$.

In various embodiments, flexible circuit board 290 further includes flex circuit fingers $271_{1-3}$ which extend distally from the body of the flexible circuit board. Microelectrodes $207_{1-3}$ are positioned on each of the flex circuit fingers $271_{1-3}$. In various embodiments, the microelectrodes $207_{1-3}$ are encompassed by an insulative layer $208_{1-3}$. As discussed above, this insulative layer insulates the microelectrodes from a conductive tip shell. These microelectrodes, when extending through the conductive shell, may collect electrophysiology data related to tissue (e.g., myocardial tissue) in contact with (or in close proximity to) the conductive shell/electrodes. This electrophysiology data may then be communicated via traces to one or more solder pads 293 on the connectors 292 of the flexible circuit 240.

The flex circuit fingers $271_{1-3}$ and thereby the microelectrodes $207_{1-3}$ may be secured to the distal tip of a tip insert via one or more securing mounts $274_{1-3}$.

To facilitate electrical and thermal coupling between thermocouples $241_{1-N}$ and $244_{1-N}$, and an inner surface of a conductive shell, the thermocouples may be directly coupled to the conductive shell. Thereby obviating any precise fitting required between the thermocouples and the conductive shell. In various embodiments consistent with the present disclosure, a quick thermal response of the thermocouples is desirable to provide an ablation control system with control inputs with as little lag as possible. Slow thermal response of the thermocouples may cause over ablation of tissue, for example.

As discussed in more detail in relation to FIGS. 2D-2G (above), when flexible circuit 240 is wrapped around a tip insert, distal thermocouples $244_{1-N}$ form a first circumferentially-extending ring positioned near a tip of the catheter. Similarly, proximal thermocouples $241_{1-N}$, form a second circumferentially-extending ring positioned near a proximal end of the tip insert.

It is to be understood that various circuit board layouts may be utilized to facilitate application specific design constraints in various flexible circuit 240 designs, consistent with the present disclosure. For example, to limit circuit board area, additional PCB layers may be added where the Z-dimension of a given application allows. Similarly, more or less connectors 292 may be implemented.

In various embodiments, the flexible circuit board 290 may include three layers: a copper layer at a top surface, an intermediate polyimide layer, and a constantan layer opposite the cooper layer. Each of the thermocouples $241_{1-N}$ and $244_{1-N}$ may be formed by drilling a via through the copper, polyimide, and constantan layers, and through plating the via with copper. Various thermocouple designs and manufacturing methods are well known in the art and may be applied hereto. Either side of the thermocouple is then electrically coupled to a trace on its respective layer. The voltage across the two traces may be compared, and the resulting voltage change is indicative of a temperature of a conductive shell thermally coupled to the thermocouple. In various applications, including ablation therapies, as the conductive shell is in direct contact with tissue being ablated, efficacy of an ablation therapy may be surmised.

In the present embodiment, flexible circuit 240 is designed to facilitate individual addressability of each of the thermocouples $241_{1-N}$ and $244_{1-N}$, and electrical contacts $293_{1-N}$. In more simplified embodiments, the thermocouples $244_{1-N}$ in a distal circumferential ring may be electrically coupled in parallel to effectively facilitate temperature averaging of the distal thermocouples, and to minimize printed circuit board size. Such an embodiment may be particularly useful in applications where determining a tissue contact point along a circumference of the ablation catheter is not necessary. The present embodiment may also limit the effect of minute hot zones on an ablation control system.

Each of the flex circuit fingers $272_{1-3}$ and $273_{1-3}$ facilitate positive positioning of the flexible circuit board when assembled to a tip insert which has mating channel features, thereby preventing movement of the flexible circuit board relative to the tip insert. Such movement may otherwise affect thermal coupling of the thermocouples to an inner surface of a conductive shell.

In some embodiments of flexible circuit 240, a top copper layer is placed above the two other layers of the flexible circuit board 290—polyimide, and constantan layers. Signal traces, printed on the top copper layer, which are electrically coupled to a hot junction for each of the thermocouples. As is well known in the arts, thermocouples typically comprise two dissimilar metals joined together at respective ends of the dissimilar metals. The end of the thermocouple placed into thermal contact with a hot object is called the hot junction, while the opposite end, which is disposed to a base-line temperature within the tip insert, is a cold junction. The hot junction in the top copper layer and the cold junction in the constantan layer are electrically coupled to one another through the polyimide layer. When a catheter tip, consistent with the present embodiment, is placed against a warm object, such as myocardial tissue being ablated by radio frequencies, a voltage difference across the hot and cold junctions develops. The voltage difference is correlated with a temperature of the hot junction. The materials of the hot and cold junctions may include one or more of the following materials: iron, nickel, copper, chromium, aluminum, platinum, rhodium, alloys of any of the above, and other metals with high conductivity.

In the embodiment of FIG. 2H, all of the cold junctions may be electrically interconnected, and effectively function as a common ground for each of the thermocouples. By electrically interconnecting each of the electrical traces extending from the cold junctions, the number of common connector pads $293_{1-N}$ may be greatly reduced. As is envisioned in the present embodiment, the common ground for all of the thermocouples would require only a single connector pad, reducing circuit board 290 size and complexity.

Figure 3A:
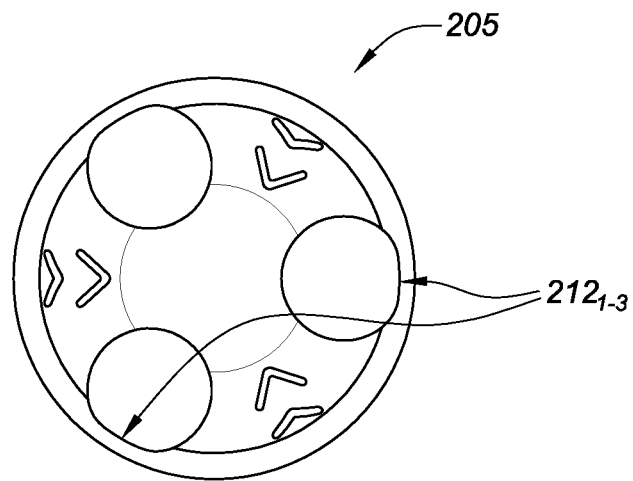
FIG. 3A is a bottom view of a conductive tip shell of an ablation catheter, consistent with various aspects of the present disclosure.
Figure 3B:
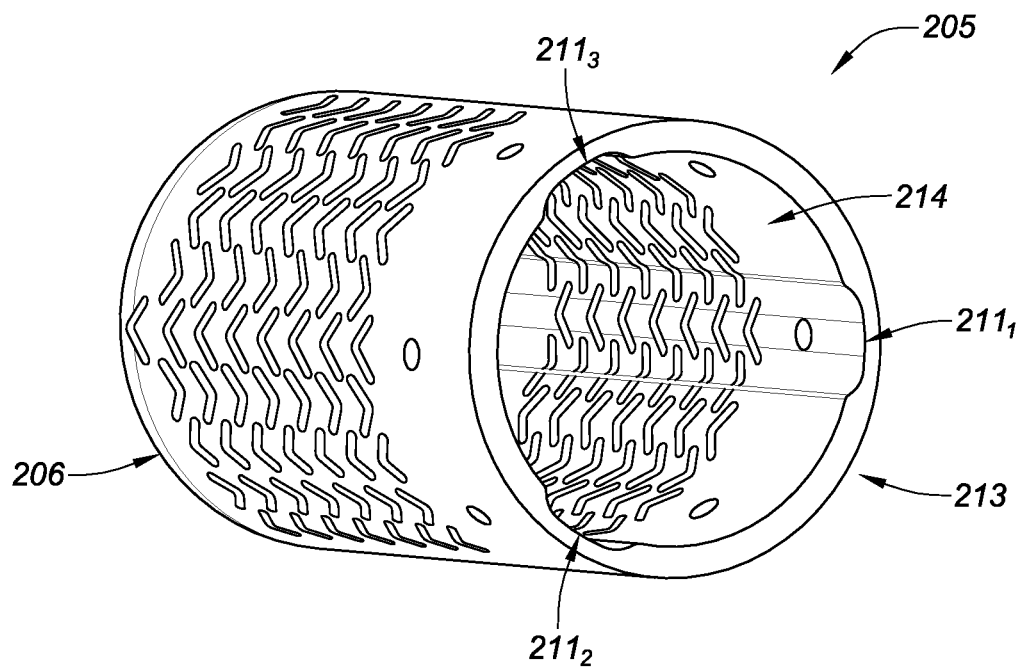
FIG. 3B is a isometric bottom view of the conductive tip shell of FIG. 3A, consistent with various aspects of the present disclosure.

FIG. 3A is a bottom view of a conductive tip shell 205 of an ablation catheter, and FIG. 3B is an isometric bottom view of the conductive tip shell 205 of FIG. 3A, consistent with various aspects of the present disclosure. To facilitate the radially extended electrophysiology electrodes of the embodiment disclosed in FIGS. 2A-C, channels $211_{1-3}$ are cut into an inner surface 214 of the conductive tip shell 205. The limit to the depth of the channels, and the corresponding radial positioning of the electrodes, is the point at which the structural integrity of the conductive tip shell is compromised by cutting the channel any deeper into the inner surface 214.

During assembly of a distal tip portion of the ablation catheter, the tip insert sub-assembly is inserted into a proximal end 213 of the tip shell until making contact with a distal end 206. The channels $211_{1-3}$ provide clearance for the electrophysiology electrodes mounted on the tip insert sub-assembly. When fully mated with the tip shell, the electrophysiology electrodes of the tip insert sub-assembly may extend into and/or through electrode apertures $212_{1-3}$ of the tip shell. In the embodiment of FIGS. 2A-C, a sensing surface of the electrodes are mounted flush with an exterior surface of the tip shell. In yet other embodiments, the sensing surface of the electrodes may protrude from the exterior surface of the tip shell.

Figure 4A:
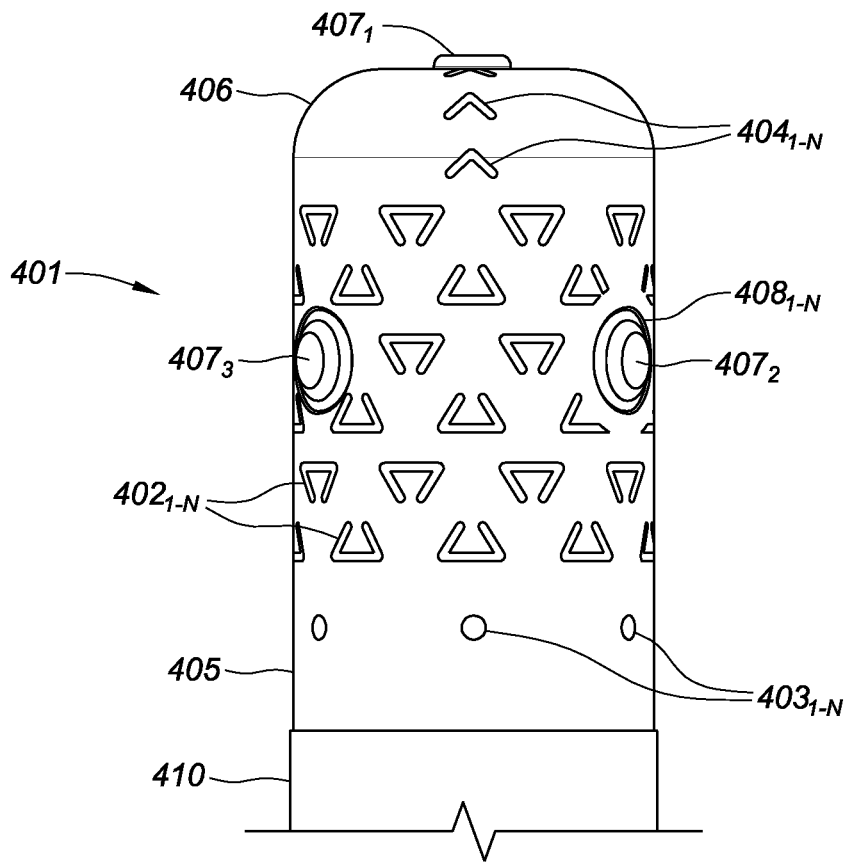
FIG. 4A is a side view of a distal tip portion of an ablation catheter, consistent with various aspects of the present disclosure.
Figure 4B:
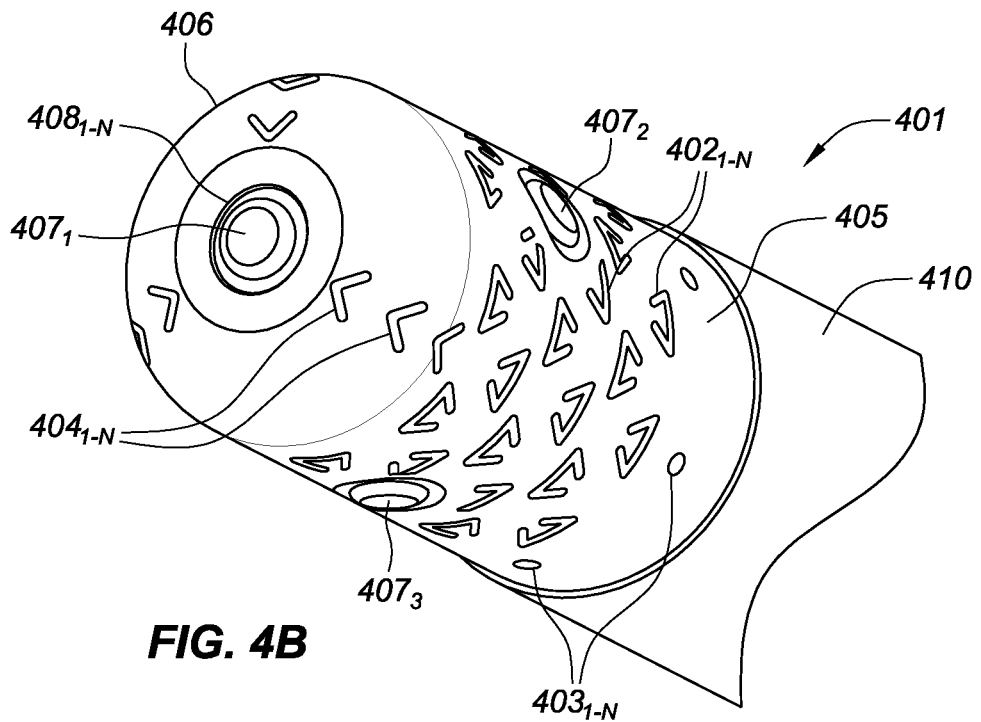
FIG. 4B is a isometric top view of the distal tip portion of FIG. 4A, consistent with various aspects of the present disclosure.

FIG. 4A is a side view of a distal tip portion 401 of an ablation catheter, and FIG. 4B is an isometric top view of the distal tip portion 401 of FIG. 4A, consistent with various aspects of the present disclosure. As shown in FIGS. 4A and 4B, the distal tip portion 401 includes a conductive tip shell 405 which is coupled to a distal end of catheter shaft 410. A number of electrophysiology electrodes $407_{1-N}$ extend through the conductive tip shell. In the present embodiment, a sensing surface of each of the electrodes extends past the exterior surface of the tip shell. A first electrode $407_1$ is aligned with a longitudinal axis of the catheter shaft and extends through a distal tip 406 of the conductive shell. A plurality of other electrodes $407_{2-N}$ may be circumferentially distributed about an outer diameter of the conductive tip shell 405. In the present embodiment, the plurality of other electrodes $407_{2-N}$ comprise a single ring of electrodes centrally located along a length of the conductive tip shell 405. The electrodes are electrically isolated from the tip shell by an insulative layer $408_{1-N}$ which circumferentially extends between each electrode and the conductive tip shell 405.

The conductive tip shell 405 includes a plurality of irrigation ports which are distributed both longitudinally and circumferentially. The plurality of irrigation ports may include a first plurality $402_{1-N}$, a second plurality $403_{1-N}$, and a third plurality $404_{1-N}$. The first plurality $402_{1-N}$, in the present embodiment, are partial-triangles in interleaving distal and proximal facing columns. The rows extending circumferentially about a diameter of the conductive tip shell 405. As discussed in reference to FIGS. 1A-C, the first plurality of irrigation ports may also affect the structural integrity of the distal tip portion 401 to facilitate flexure of the distal tip portion when placed into contact with myocardial tissue, for example. The second plurality of irrigation ports 403$_{1-N}$ are positioned proximal the first plurality of irrigation ports and extend circumferentially about the outer diameter of the conductive tip shell 405 in a single ring. In the present embodiment, the second plurality of irrigation ports are circular apertures. The third plurality of irrigation ports 404$_{1-N}$ may be chevrons which extend from an outer diameter of the conductive tip shell to a distal tip 406 in one or more longitudinally extending columns toward a distal tip electrode 407$_1$ (also referred to as the first electrode). In addition to their function as irrigation ports, the various irrigation ports may also facilitate an increased frictional coefficient between the distal tip portion 401 and myocardial tissue in contact therewith, preventing unintentional movement of the ablation catheter during ablation therapy.

While FIGS. 4A and 4B exemplify an embodiment with one specific pattern for each of the first, second, and third plurality of irrigation ports, a skilled artisan would appreciate that various modification to the illustrated pattern may be readily achieved, as well as various irrigation port shapes to achieve the desired irrigation dispersion characteristics, distal tip flexure, and tip-tissue contact characteristics.

Figure 5A:
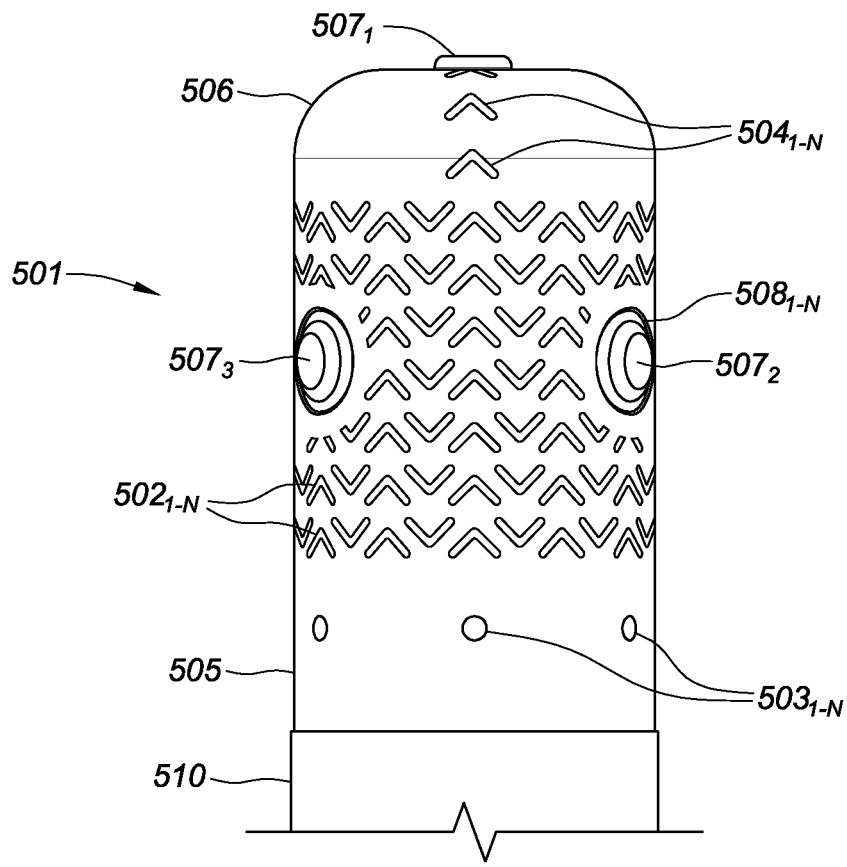
FIG. 5A is a side view of a distal tip portion of an ablation catheter, consistent with various aspects of the present disclosure.
Figure 5B:
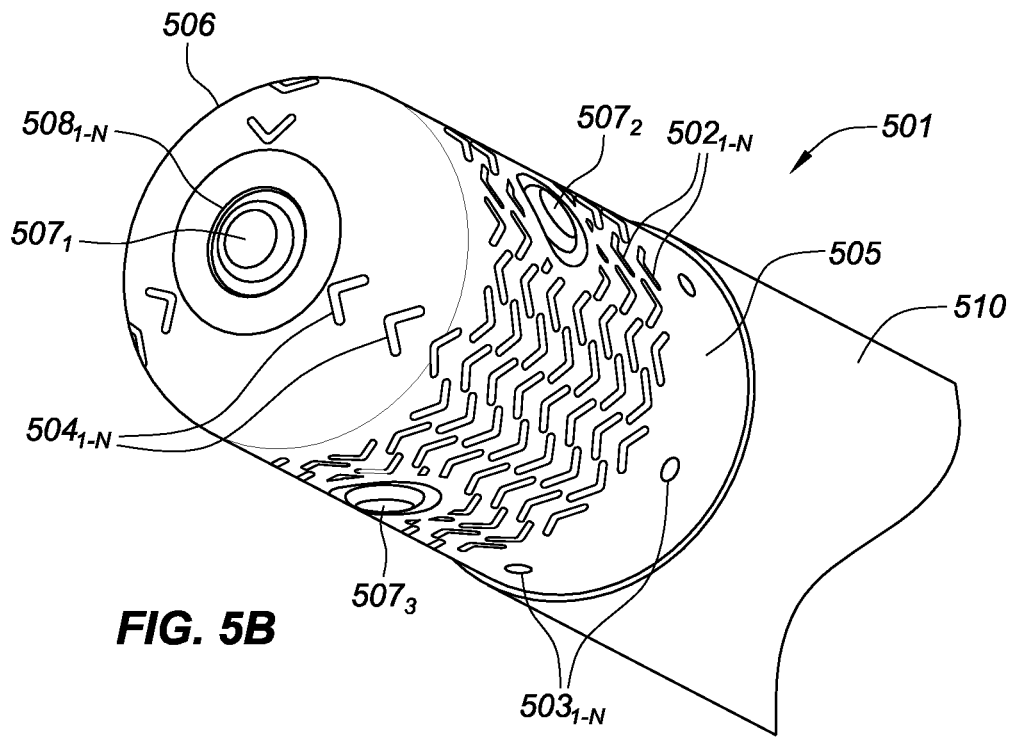
FIG. 5B is a isometric top view of the distal tip portion of FIG. 5A, consistent with various aspects of the present disclosure.

FIG. 5A is a side view of a distal tip portion 501 of an ablation catheter, and FIG. 5B is an isometric top view of the distal tip portion 501 of FIG. 5A, consistent with various aspects of the present disclosure. The embodiment of FIGS. 5A and 5B are similar to the distal tip portion described in reference to FIGS. 1A-1C, except for the relative placement of electrophysiology electrodes. As shown in FIGS. 5A and 5B, the distal tip portion 501 includes a conductive tip shell 505 which is coupled to a distal end of catheter shaft 510. A number of electrophysiology electrodes 507$_{1-N}$ extend through the conductive tip shell. In the present embodiment, a sensing surface of each of the electrodes extends past the exterior surface of the tip shell. A first electrode 507$_1$ is aligned with a longitudinal axis of the catheter shaft and extends through a distal tip 506 of the conductive shell. A plurality of other electrodes 507$_{2-N}$ may be circumferentially distributed about an outer diameter of the conductive tip shell 505. In the present embodiments, the plurality of other electrodes 507$_{2-N}$ comprise a single ring of electrodes centrally located along a length of the conductive tip shell 505. The electrodes are electrically isolated from the tip shell by an insulative layer 508$_{1-N}$ which circumferentially extends about each electrode.

The conductive tip shell 505 includes a plurality of irrigation ports which are distributed both longitudinally and circumferentially. The plurality of irrigation ports may include a first plurality 502$_{1-N}$, a second plurality 503$_{1-N}$, and a third plurality 504$_{1-N}$. The plurality of irrigation ports are as described in reference to FIGS. 4A and 4B, except for the shape of the irrigation features which are as described in reference to FIGS. 1A-C.

Figure 6A:
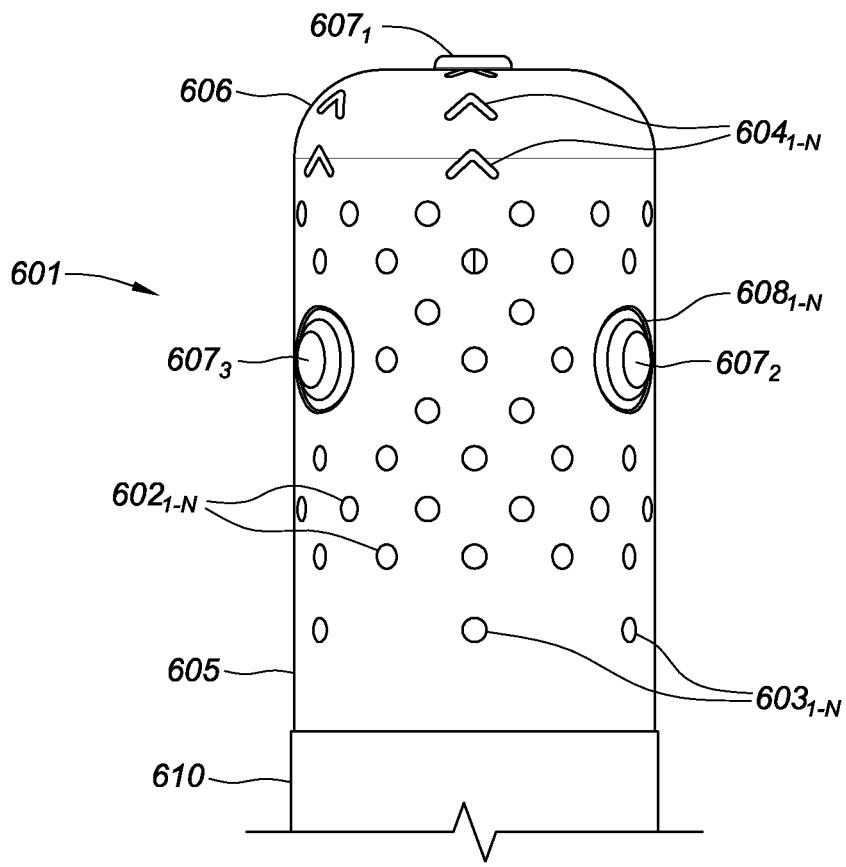
FIG. 6A is a side view of a distal tip portion of an ablation catheter, consistent with various aspects of the present disclosure.
Figure 6B:
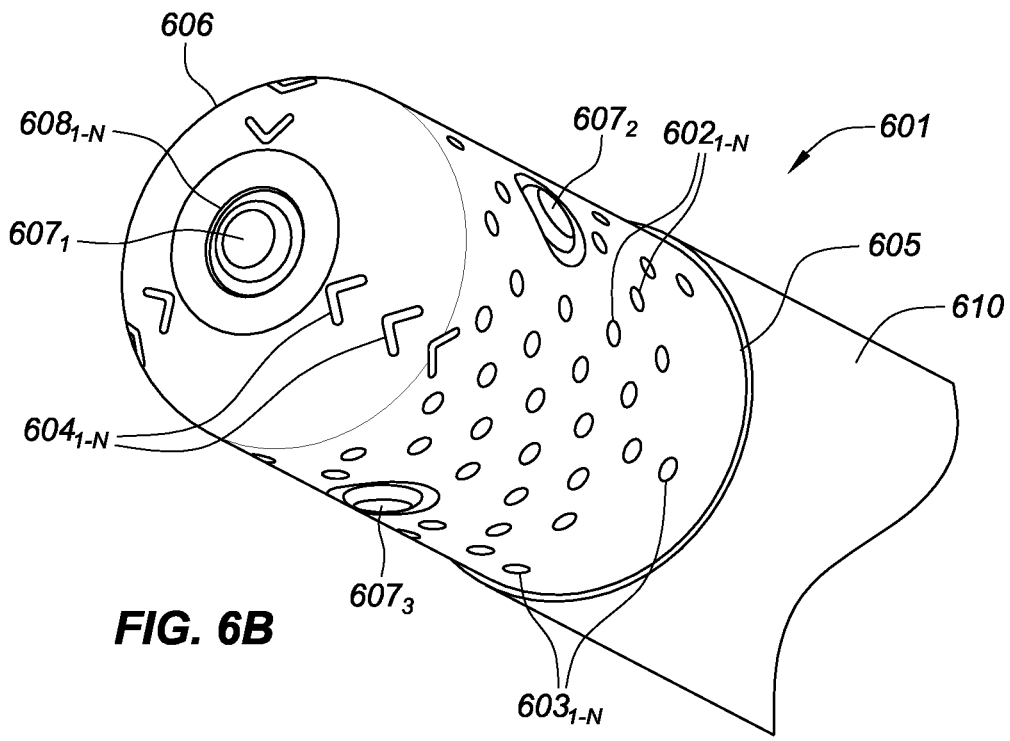
FIG. 6B is a isometric top view of the distal tip portion of FIG. 6A, consistent with various aspects of the present disclosure.

FIG. 6A is a side view of a distal tip portion of an ablation catheter, and FIG. 6B is an isometric top view of the distal tip portion of FIG. 6A, consistent with various aspects of the present disclosure. The embodiment of FIGS. 6A and 6B are similar to the distal tip portion described in reference to FIGS. 4A, 4B, 5A, and 5B, except for the shape of the first plurality of irrigation ports 602$_{1-N}$ which are circular apertures, the same as the second plurality of irrigation ports 603$_{1-N}$. However, in the present embodiment, the patterning of the irrigation ports in the first and second plurality of irrigation ports varies. Specifically, the radial spacing between the second plurality of irrigation ports is greater than the first plurality of irrigation ports.

Similar to FIGS. 5A and 5B, distal tip portion 601 of FIGS. 6A and 6B include a conductive tip shell 605 which is coupled to a distal end of catheter shaft 610. A number of electrophysiology electrodes 607$_{1-N}$ extend through the conductive tip shell. In the present embodiment, a sensing surface of each of the electrodes extends past the exterior surface of the tip shell. A first electrode 607$_1$ is aligned with a longitudinal axis of the catheter shaft and extends through a distal tip 606 of the conductive shell. A plurality of other electrodes 607$_{2-N}$ may be circumferentially distributed about an outer diameter of the conductive tip shell 605. In the present embodiment, the plurality of other electrodes 607$_{2-N}$ comprise a single ring of electrodes centrally located along a length of the conductive tip shell 605. The electrodes are electrically isolated from the tip shell by an insulative layer 608$_{1-N}$ which circumferentially extends about each electrode.

FIG. 7A is a side view of a distal tip portion 701 of an ablation catheter, FIG. 7B is an isometric top view of the distal tip portion 701 of FIG. 7A, and FIG. 7C is a top view of the distal tip portion 701 of FIG. 7A, consistent with various aspects of the present disclosure. As shown in FIGS. 7A-C, The embodiment of FIGS. 7A-C are similar to the distal tip portion described in reference to FIGS. 6A and 6B, except for the size of the first and second plurality of irrigation ports (702$_{1-N}$ and 703$_{1-N}$, respectively) which are smaller circular apertures then those shown in reference to FIGS. 6A and 6B. However, the patterning of the first and second plurality of irrigation ports is maintained.

Similar to FIGS. 6A and 6B, distal tip portion 701 of FIGS. 7A and 7B includes a conductive tip shell 705 which is coupled to a distal end of catheter shaft 710. A number of electrophysiology electrodes 707$_{1-N}$ extend through the conductive tip shell. In the present embodiment, a sensing surface of each of the electrodes extends past the exterior surface of the tip shell. A first electrode 707$_1$ is aligned with a longitudinal axis of the catheter shaft and extends through a distal tip 706 of the conductive shell. A plurality of other electrodes 707$_{2-N}$ may be circumferentially distributed about an outer diameter of the conductive tip shell 705. In the present embodiment, the plurality of other electrodes 707$_{2-N}$ comprise a single ring of electrodes centrally located along a length of the conductive tip shell 705. The electrodes are electrically isolated from the tip shell by an insulative layer 708$_{1-N}$ which circumferentially extends about each electrode.

Similar to many of the other embodiments, a third plurality of irrigation ports 704$_{1-N}$ are chevrons which extend longitudinally in one or more columns toward the first electrode 707$_1$ on distal tip 706. The third plurality of irrigation ports providing for desirable irrigation in and around the distal tip and the first electrode thereon. As a skilled artisan would appreciate, the specific patterning, location, size, and shape of the plurality of irrigation ports on distal tip portion 701 may vary based on a given clinical application and/or desired therapeutic outcome.

FIG. 8A is an isometric side view of an insert 801 for a distal tip portion of an ablation catheter, FIG. 8B is a side view of the insert 801 of FIG. 8A, and FIG. 8C is a top view of the insert 801 of FIG. 8A, consistent with various aspects of the present disclosure. The tip insert 801 is configured for coupling to a distal end of a catheter shaft. A flexible electronic circuit further coupled (circumferentially in some embodiments) about the tip insert. In the present embodiment, the flex circuit may include a plurality of temperature sensors which when the flex circuit is coupled to the tip insert would be positioned in proximal and distal rings about the tip insert 801. The proximal and distal rings of temperature sensors are designed to facilitate high thermal sensitivity of the conductive tip shell. The tip insert, as shown in FIGS. 8A-C, is designed to pair with a flex circuit including flex circuit fingers with one or more temperature sensors mounted on each of these fingers. These fingers during assembly are then mated to complimentary mounting features ($832_{1-N}$ and $833_{1-N}$) on the tip insert 801, and the body of the flex circuit extending circumferentially about and coupling to outer surface 834 of the tip insert. When the conductive tip shell is mated to the tip insert 801, the temperature sensors may be sandwiched between the tip insert and tip shell (and not require further securing); however, in some embodiments the temperature sensors and/or flex circuit fingers may be further secured by adhesive or some other method well known in the art. In yet further more specific embodiments, a conductive paste may be placed between the temperature sensors and the tip shell to further facilitate thermal transfer there between.

While the present embodiment is directed to a tip insert 801 which facilitates a high thermal sensitivity ablation catheter with two rings of six temperature sensors each, various other configurations are readily envisioned. For example, more or less temperature sensors in each row, unevenly distributed temperature sensors in a particular ring, and one or more rings distributed along a length of the distal tip portion of the ablation catheter. Moreover, in some embodiments it may be desirable to place one or more temperature sensors on the distal tip of the ablation catheter (as shown in FIGS. 8A and 8C). Similar to the other temperature sensors discussed above, the distal tip temperature sensor may be installed within distal channel 838 of the tip insert via a flex circuit finger.

Unlike some of the previous ablation catheter embodiments presented herein, the present embodiment does not include a distally oriented electrophysiology electrode. Instead, in the present embodiment a trio of electrophysiology electrodes are circumferentially distributed about an outer circumference of the tip insert. Each of the electrodes are configured to be mounted to electrode pedestals $831_{1-3}$ which extend radially outward from an outer surface 834 of the tip insert 801 and facilitate precise positioning of the electrodes. The height of the pedestal determined based on the radius of the conductive tip shell, the thickness of the respective electrodes, and the desired placement of the sensing surface of the electrode relative to an outer surface of the tip shell (e.g., flush mounted, or extending out past the outer surface of the tip shell).

Tip insert 801 further facilitates delivery of irrigant to the various irrigation ports in the conductive tip shell (when assembled). The tip insert receives irrigant through a central irrigation lumen in the catheter shaft. The irrigant enters a central lumen 839 at a proximal end 803 of the tip insert (shown in FIGS. 8D-F) and is circumferentially distributed about the tip insert via three irrigation nozzles $835_{1-3}$. After exiting the irrigation nozzles $835_{1-3}$, the irrigant flows distally between the flex circuit and an inner surface of a conductive tip shell (when the tip insert is assembled with the rest of the ablation catheter tip) before extending radially out of the plurality of irrigation ports in the tip shell. To facilitate the flow of irrigant to a distal tip 802 of the tip insert, the tip insert includes irrigant channels $836_{1-3}$ which deliver a portion of the irrigant to distally-facing irrigant ports in the tip shell.

Figure 8F:
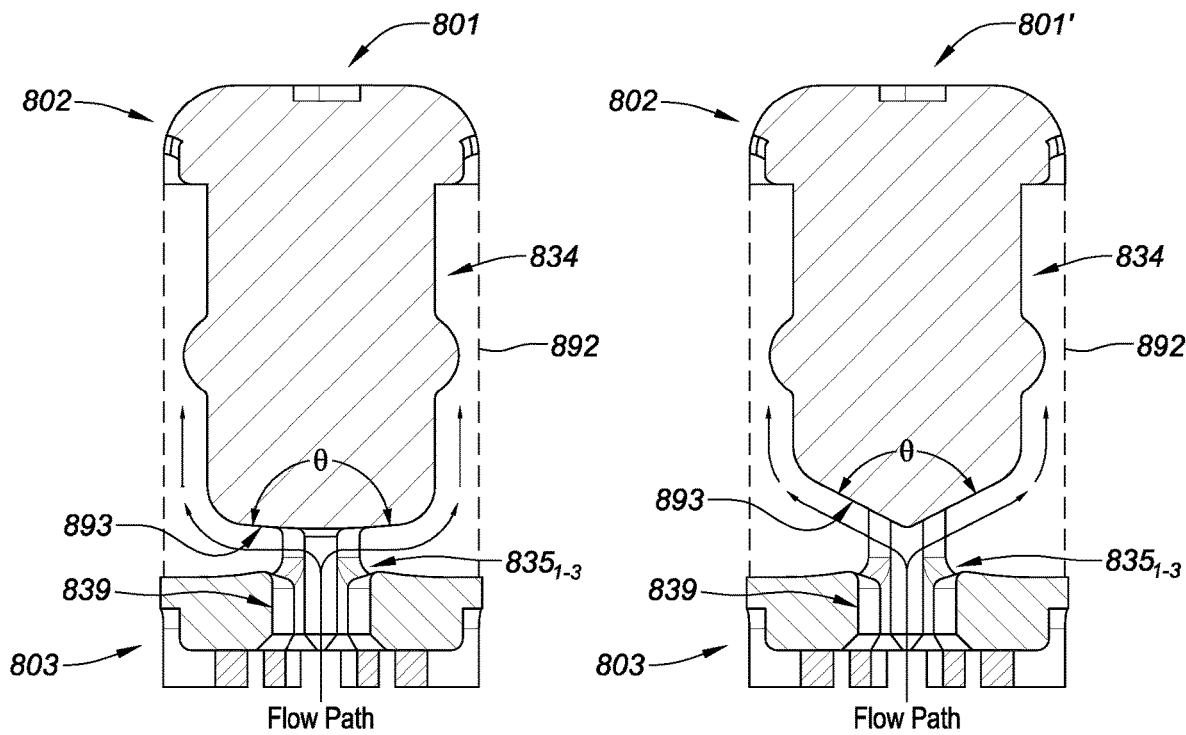
FIG. 8F is a cross-sectional side view of a third embodiment of the insert of FIG. 8A, consistent with various aspects of the present disclosure.
Figure 8F:
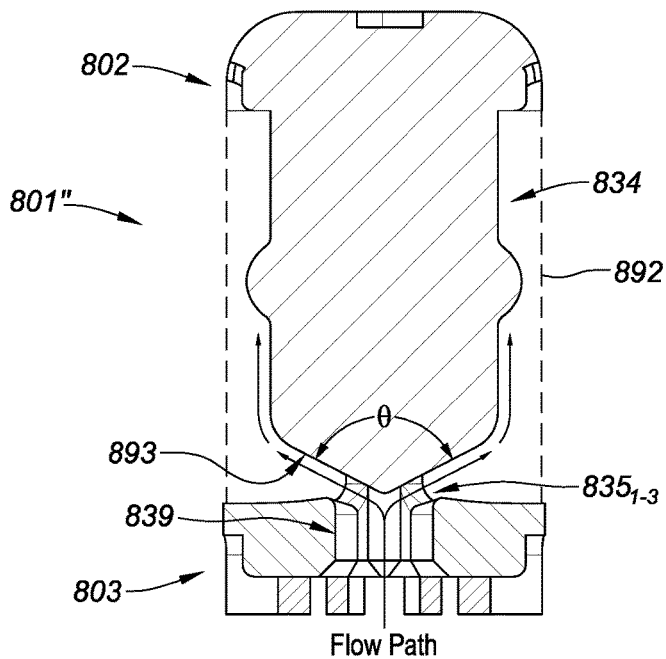

In FIGS. 8D-F, several embodiments of a tip insert are shown. The differences including the angle of incidence of the incoming irrigant (due to the deflecting surface 893), and the height of the three irrigation nozzles $835_{1-3}$. These aspects affect how the irrigant flows through the tip insert and the efficacy and uniformness of proximal tip irrigation.

FIG. 8D is a cross-sectional side view of a first embodiment 801 of the insert of FIG. 8A, consistent with various aspects of the present disclosure. As shown in FIG. 8D, an irrigant flow path through the tip insert extends from a proximal end 803 to a distal end 802 of the tip insert via a central lumen 839 before being diverted radially outward via three irrigation nozzles $835_{1-3}$ and a deflecting surface 893. After exiting the three irrigation nozzles, the irrigant flow extends distally between an outer surface 834 of the tip insert 801 and an inner surface 892 of a conductive tip shell (shown as a dotted line).

In FIG. 8D, a deflecting surface 893 of tip insert 801 has a $\Theta$ (theta) angle of approximately 180° and an irrigant nozzle vertical opening of a medium dimension. As shown by the illustrative irrigant flow path, the irrigant extends through the central lumen and is forced radially outward by the deflecting surface 893. The three irrigation nozzles $835_{1-3}$, in conjunction with the deflecting surface 893 further force the irrigant into a primarily radial flow until the flow contacts outer surface 892 of a conductive tip shell and again flows distally. In the present embodiment, the exit velocity from the three irrigation nozzles $835_{1-3}$ is greater than that of FIG. 8E, and less than the exit velocity of FIG. 8F.

FIG. 8E is a cross-sectional side view of a second embodiment 801' of the insert of FIG. 8A, consistent with various aspects of the present disclosure. In FIG. 8E, a deflecting surface 893 of tip insert 801 has a $\Theta$ (theta) angle of approximately 120° and an irrigant nozzle vertical opening of a large dimension. As shown by the illustrative irrigant flow path, the irrigant extends through the central lumen and is forced radially outward by the deflecting surface 893. The three irrigation nozzles $835_{1-3}$, in conjunction with deflecting surface 893, force the irrigant into a flow vector including a combination of radial and longitudinal flow until the flow contacts outer surface 892 of a conductive tip shell and again flows primarily longitudinally to a distal end 802 of the tip insert.

FIG. 8F is a cross-sectional side view of a third embodiment 801" of the insert of FIG. 8A, consistent with various aspects of the present disclosure. In FIG. 8F, a deflecting surface 893 of tip insert 801 has a $\Theta$ (theta) angle of approximately 120° and an irrigant nozzle vertical opening of a small dimension. As shown by the illustrative irrigant flow path, the irrigant extends through the central lumen and is forced radially outward by the deflecting surface 893. The three irrigation nozzles $835_{1-3}$, in conjunction with deflecting surface 893, force the irrigant into a flow vector including a combination of radial and longitudinal flow until the flow contacts outer surface 892 of a conductive tip shell and again flows primarily longitudinally to a distal end 802 of the tip insert. However, due to the decreased dimension of the irrigation nozzles, relative to FIG. 8E, the irrigant flow exhibits increased velocity along the tip insert.

Figure 9A:
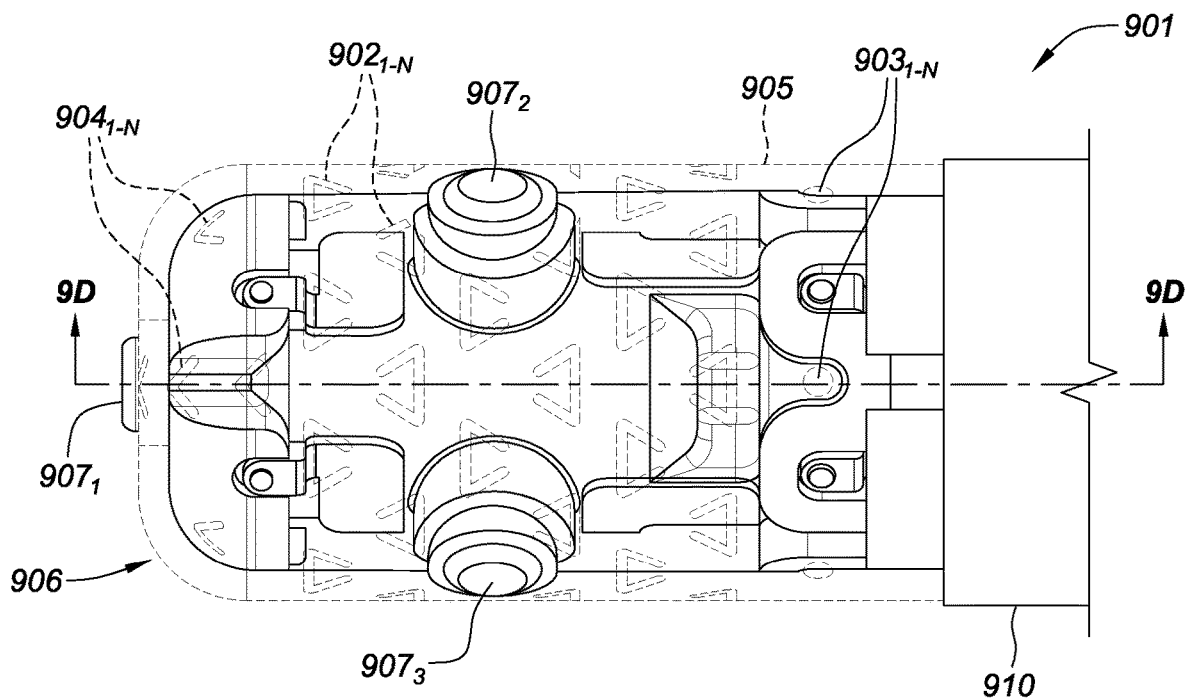
FIG. 9A is a side view of a distal tip portion of an ablation catheter, consistent with various aspects of the present disclosure.
Figure 9B:
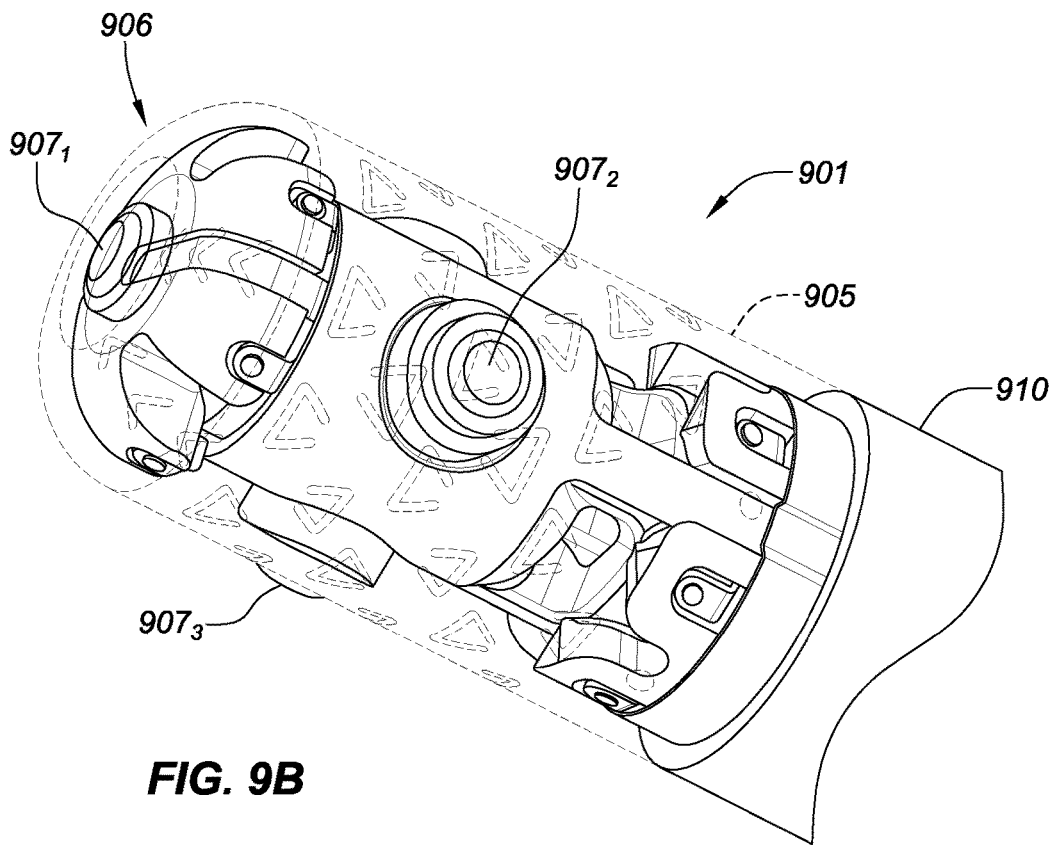
FIG. 9B is a isometric top view of the distal tip portion of FIG. 9A, consistent with various aspects of the present disclosure.

FIG. 9A is a side view of a distal tip portion 901 of an ablation catheter, and FIG. 9B is an isometric top view of the distal tip portion of FIG. 9A, consistent with various aspects of the present disclosure. The distal tip portion 901 of the ablation catheter includes a conductive tip shell 905 (shown in phantom) which is coupled to a distal end of catheter shaft 910. In various embodiments of the present disclosure, the conductive tip shell may be configured to ablate myocardial tissue (or other tissue) using radio-frequency energy which is transmitted to the tissue via the conductive tip shell 905. To facilitate enhanced tissue contact, the conductive tip shell may be flexible and/or (partially) deformable. For example, as shown in FIGS. 9A and 9B, the conductive tip shell 905 includes a plurality of partial-triangle features $902_{1-N}$, in interleaving distal and proximal facing columns, which extend through the tip shell. Further, the columns of partial-triangle features extend circumferentially about an outer diameter of the conductive tip shell. The plurality of partial-triangle features $902_{1-N}$ function to both reduce the structural rigidity of the conductive tip shell 105 to maximize tissue contact, and/or to facilitate delivery of irrigation fluid into proximity with target tissue.

As further shown in FIGS. 9A and 9B, one or more columns of the plurality of partial-triangle features $902_{1-N}$ may extend distally onto a distal tip 906 of the conductive tip shell 905 to further facilitate enhanced irrigation at the distal tip. In the present embodiment, three rows of chevron features $904_{1-N}$ extend distally from an outer circumference of the conductive tip shell 905 on to the distal tip 906. In the present embodiment, the chevron features $904_{1-N}$ at the distal tip 906 form three or more columns (six columns are shown in FIG. 9B) and extend toward an end in close proximity to a distal tip electrophysiology electrode $907_1$. An outer diameter of the conductive tip shell includes a plurality of electrophysiology electrodes $907_{2-4}$ that are circumferentially distributed about a longitudinal axis of the catheter shaft 910. The electrophysiology electrodes distributed about the conductive tip shell facilitate electrophysiology analysis of the tissue in contact with the distal tip portion before, during, and/or after an ablation therapy. Applicant further notes that, in various embodiments of the present disclosure, the electrodes are separate from the shell.

Figure 9C:
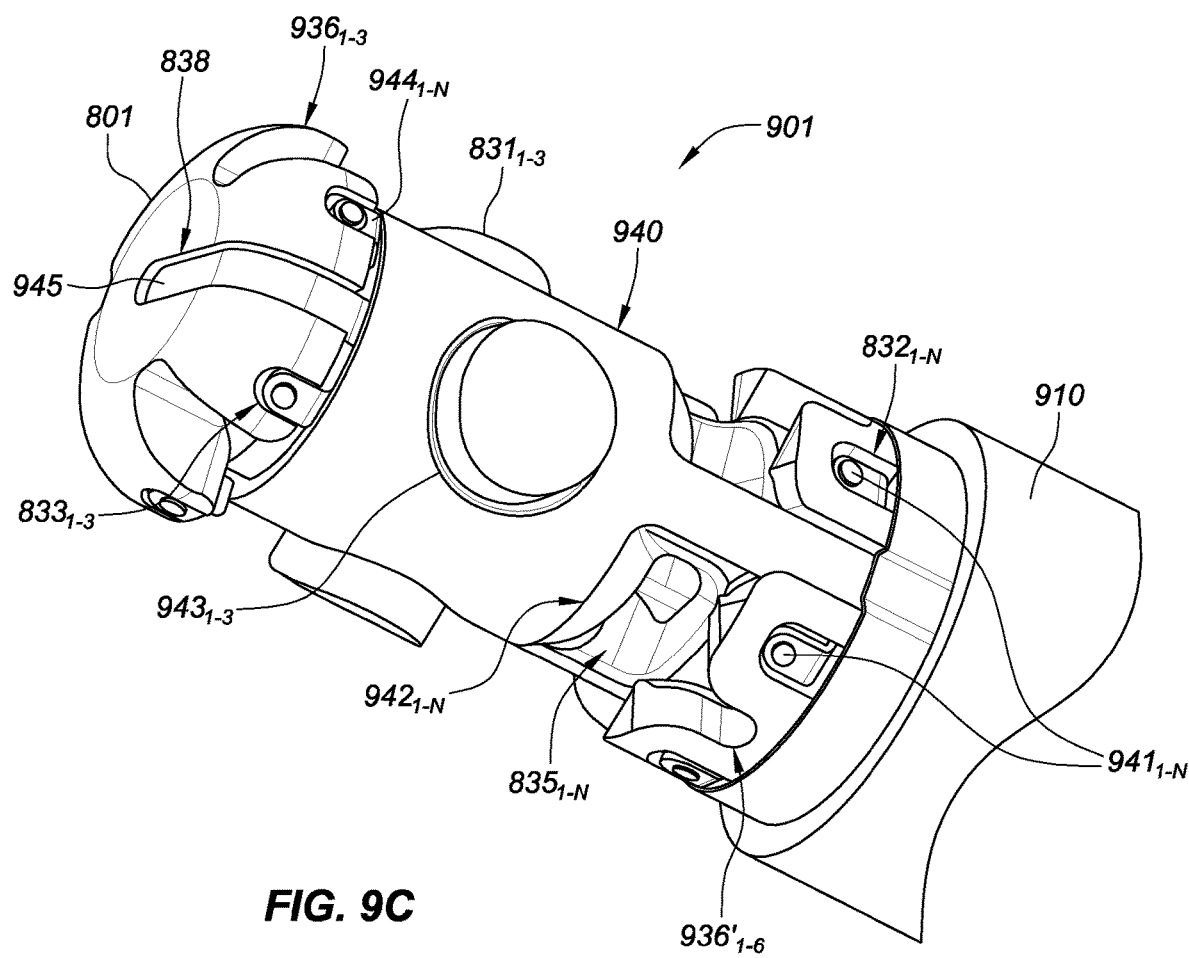
FIG. 9C is an isometric top view of the partially assembled distal tip portion of FIG. 9A, consistent with various aspects of the present disclosure.

In a distal tip portion 901 of an ablation catheter embodiment as shown in FIGS. 9A-C, a proximal portion of conductive tip shell 905 may or may not include additional irrigation apertures $903_{1-N}$. These additional irrigation apertures may be placed proximal to a coupling between the conductive tip shell and catheter shaft 910. In some embodiments, the additional irrigation apertures may not impact the structural integrity of the conductive tip shell, but instead merely function to further irrigate the conductive tip shell 905, specifically a proximal portion of the tip shell. In the present embodiment, the additional irrigation apertures $903_{1-N}$ are circular apertures which are evenly distributed about a circumference of the tip shell.

As is apparent from the various embodiments disclosed in the present application (see, e.g., FIGS. 11A-15B), while each embodiment is presented with one or more types of irrigation features (e.g., chevron, aperture, nozzle, etc.), a skilled artisan will appreciate that various combinations and patterns of these irrigation features are readily envisioned.

FIG. 9C is an isometric top view of the partially assembled distal tip portion 901 of FIG. 9A without the conductive tip shell 905, consistent with various aspects of the present disclosure. As shown in FIG. 9C, a tip insert 801 is coupled to a distal end of catheter shaft 910. A flexible electronic circuit 940 (or flex circuit) is coupled (circumferentially in some embodiments) to the tip insert 801. The flex circuit includes a plurality of temperature sensors which, in the present embodiment, are positioned in proximal and distal rings ($941_{1-N}$ and $944_{1-N}$, respectively) about the tip insert 801. The proximal and distal rings of temperature sensors facilitate high thermal sensitivity of the conductive tip shell 905 (not shown in FIG. 9C). In the present embodiment, each of the temperature sensors, which are (communicatively) coupled to the flex circuit 940, extend out on flex circuit fingers (941 and 944) and these fingers are mated to complimentary mounting features ($832_{1-N}$ and $833_{1-N}$) on the tip insert (as described in more detail in reference to FIGS. 2D-2G). When a conductive tip shell is mated to the tip insert, the temperature sensors are sandwiched between the tip insert and tip shell.

While the present embodiment discloses a high thermal sensitivity ablation catheter with two rings of six temperature sensors each, various other configurations are readily envisioned. For example, more or less temperature sensors in each row, unevenly distributed temperature sensors in a particular ring, and one or more rings distributed along a length of the distal tip portion 901 of the ablation catheter. Moreover, in some embodiments it may be desirable to place one or more distal temperature sensors 945 on a distal tip of the ablation catheter (as shown in FIG. 9C). In yet other embodiments 945 may be a contact point (e.g., solder pad) for coupling an electrophysiology electrode and/or a hybrid-type electrode/temperature sensor.

As discussed in more detail above, a distal tip portion 901 of the ablation catheter includes a plurality of electrophysiology electrodes. The radially facing electrodes are mounted to pedestals $831_{1-3}$ which extend radially from the tip insert 801. The flex circuit 940 may include cuts $943_{1-3}$ which circumferentially extend about the pedestals (when assembled) and facilitate positively positioning the flex circuit relative to the tip insert. The pedestals also facilitate precise positioning of the electrodes relative to a surface of, and openings in, the conductive tip shell.

Tip insert 801 further facilitates delivery of irrigant to the various irrigation ports in the conductive tip shell. In the present embodiment, catheter shaft 910 includes a central irrigation lumen which extends from a catheter handle to a distal end of the catheter shaft. The irrigant enters a central lumen of the tip insert and is circumferentially distributed about the tip insert via three irrigation nozzles $835_{1-3}$ and a deflecting surface 893 (as shown in, for example, FIGS. 8D-F). After exiting the irrigation nozzles $835_{1-3}$, the irrigant flows distally between the flex circuit 940 and an inner surface of a conductive tip shell 905 before extending radially out of the plurality of irrigation ports $902_{1-N}$, and/or longitudinally out of distally facing irrigation ports $904_{1-N}$. via distal irrigation channels $936_{1-3}$, and/or proximal irrigation ports $903_{1-N}$ via proximal irrigation channels $936_{1-6}$.

Figure 9D:
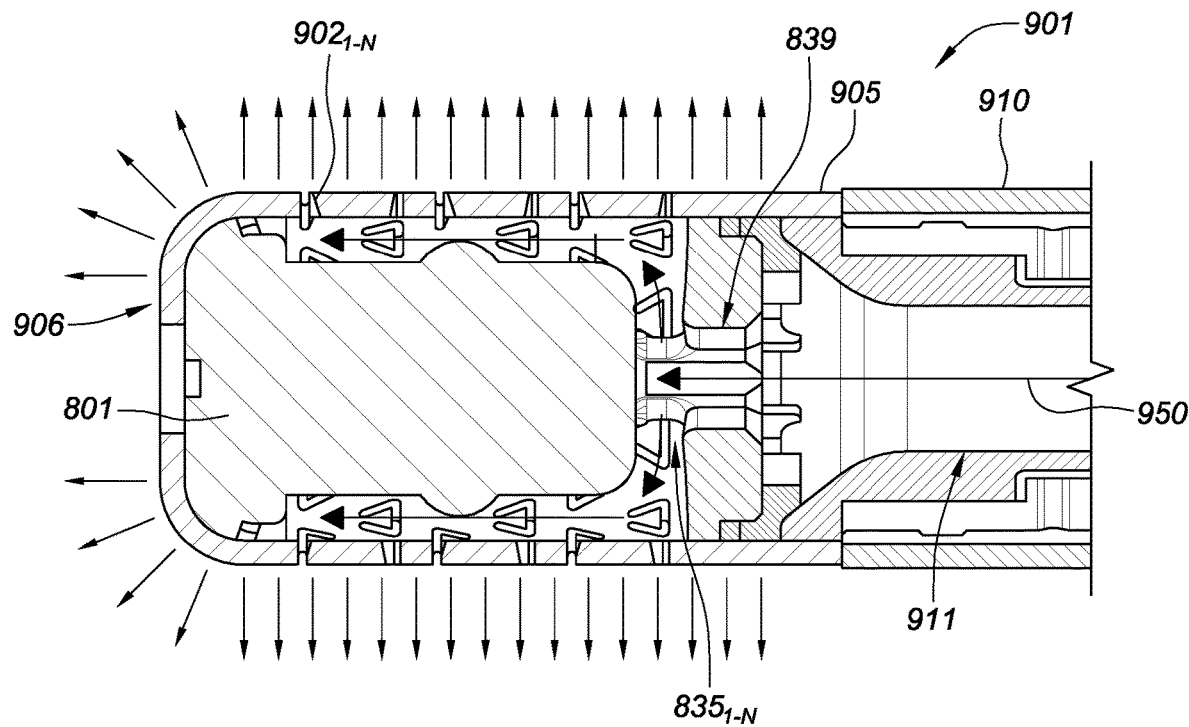
FIG. 9D is a cross-sectional side view of the distal tip portion of FIG. 9A, consistent with various aspects of the present disclosure.

FIG. 9D is a cross-sectional side view of the distal tip portion 901 of FIG. 9A, consistent with various aspects of the present disclosure. The cross-sectional side view of the distal tip portion 901 helps to illustrate irrigant flow through the distal tip portion. Irrigant flows through a central lumen 911 of catheter shaft 910 from a proximal end of the catheter shaft to a distal end. Upon arriving at the distal end of the catheter shaft the irrigant transitions into a smaller diameter central lumen 839 of tip insert 801 before being directed radially outward (relative to a longitudinal axis of the catheter shaft) via three irrigation nozzles $835_{1-3}$ and a deflecting surface 893 (as shown in, for example, FIGS. 8D-F). Upon contacting an inner surface of the tip shell 905, the irrigant flows towards a distal end 906 via a channel formed between the flex circuit and the inner surface of the conductive tip shell before extending radially out of the plurality of irrigation ports/nozzles $902_{1-N}/903_{1-N}$, and/or longitudinally out of distally facing irrigation ports $904_{1-N}$.

Applicant notes that in reference to FIG. 9D that the arrows are not scaled to indicate flow velocity or volume, but to merely visually indicate approximate irrigant flow direction.

Figure 10A:
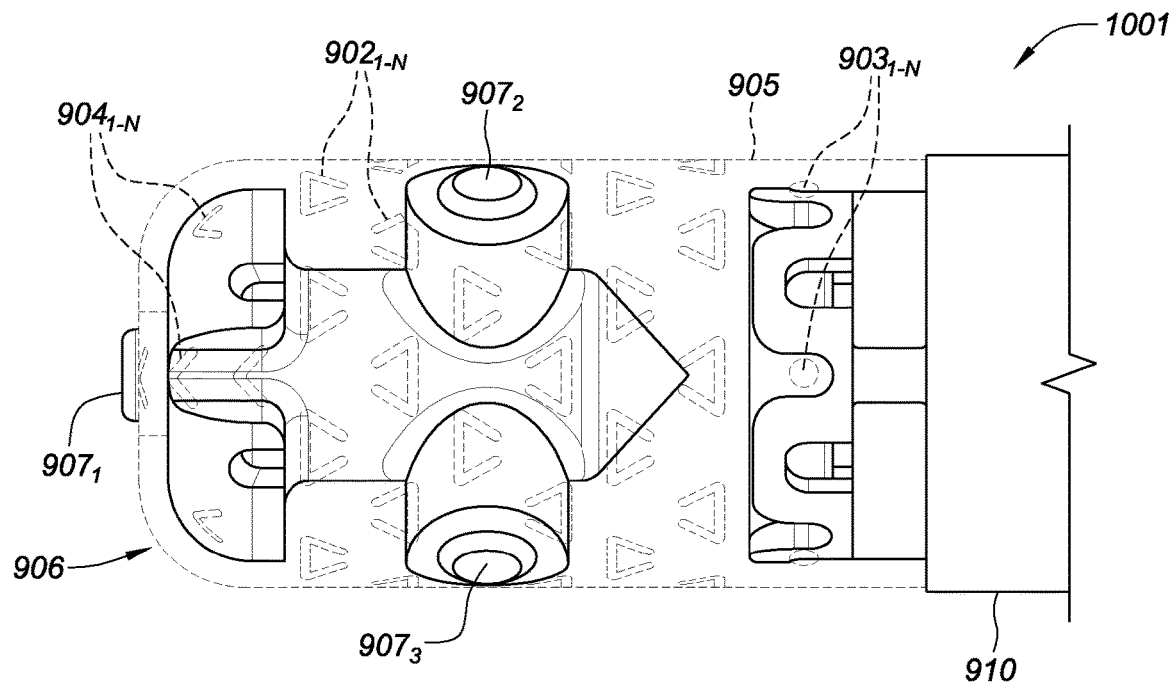
FIG. 10A is a side view of a distal tip portion of an ablation catheter, consistent with various aspects of the present disclosure.
Figure 10B:
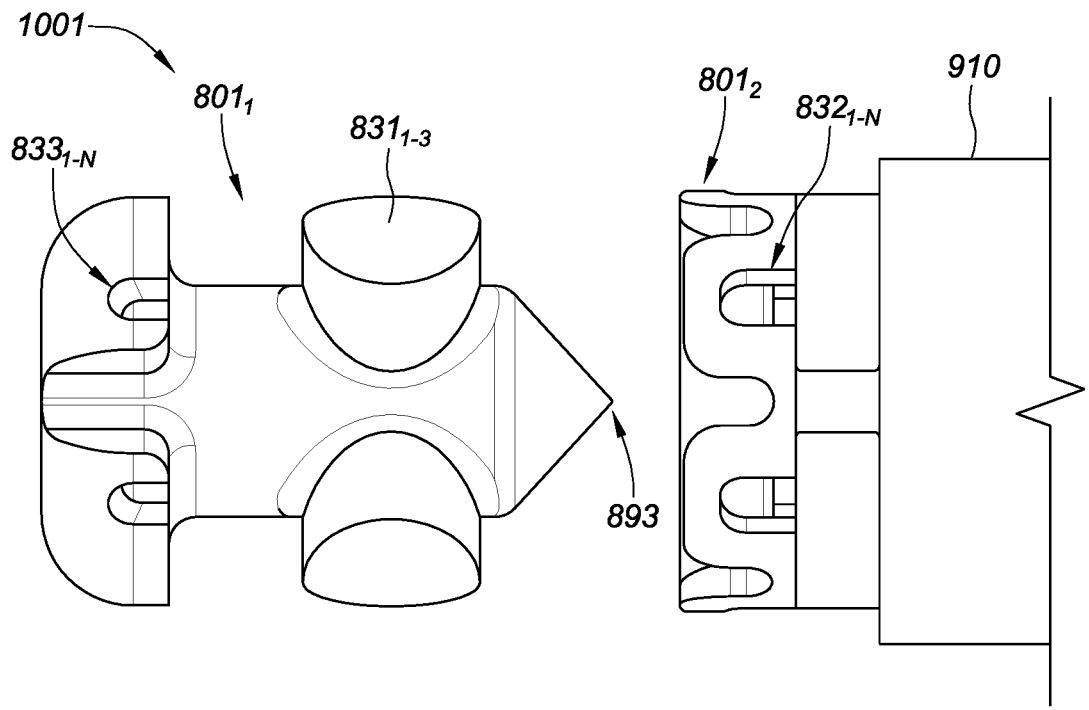
FIG. 10B is a side view of the partially assembled, distal tip portion of FIG. 10A, consistent with various aspects of the present disclosure.
Figure 10C:
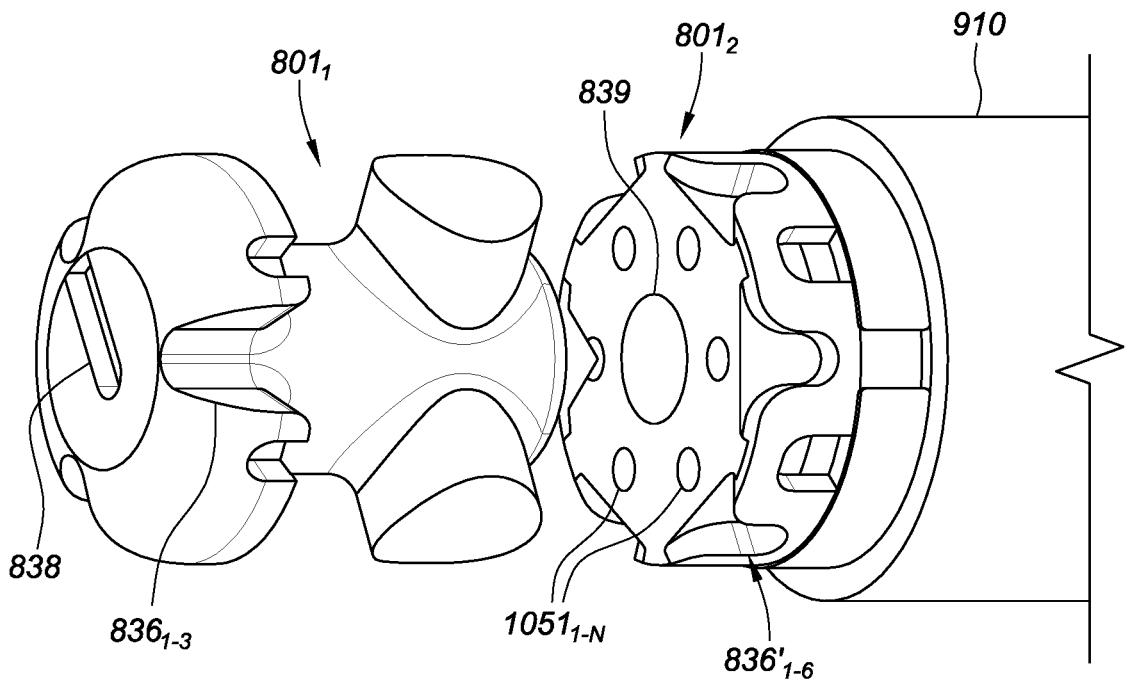
FIG. 10C is an isometric top view of the partially assembled, distal tip portion of FIG. 10A, consistent with various aspects of the present disclosure.

FIG. 10A is a side view of a distal tip portion 1001 of an ablation catheter, FIG. 10B is a side view of the partially assembled, distal tip portion 1001 of FIG. 10A, and FIG. 10C is an isometric top view of the partially assembled, distal tip portion 1001 of FIG. 10A, consistent with various aspects of the present disclosure. The distal tip portion 1001 of FIGS. 10A-C is largely similar to the embodiments described in reference to FIGS. 9A-C except that tip insert 801 of the embodiment in FIGS. 10A-C comprises two parts ($801_{1-2}$) with the conductive tip shell 905 coupling the two parts of the tip insert together. As shown in FIGS. 10B and 10C, a first (distal) portion $801_1$ of the tip insert includes a distal tip channel 838, distal irrigation channels $836_{1-3}$, electrode pedestals $831_{1-3}$, distal temperature sensor mounting features $833_{1-N}$, and a deflecting surface 893. The second (proximal) portion $801_2$ includes proximal irrigation channels $836'_{1-6}$, proximal temperature sensor mounting features $832_{1-N}$, a central irrigant lumen 839, and a plurality of lead wire lumens $1051_{1-N}$.

In the present embodiment, instead of using a flex circuit to communicatively couple the various electrodes and temperature sensors to controller circuitry, lead wires (which access the distal tip portion 1001 via the plurality of lead wire lumens $1051_{1-N}$) may be used to communicatively coupled each of the electrodes and temperature sensors to the controller circuitry.

Upon arriving at the distal end of the catheter shaft, irrigant transitions into a central lumen 839 of second (proximal) portion $801_2$ of the tip insert before being directed radially outward (relative to a longitudinal axis of the catheter shaft) via a deflecting surface 893 of first (distal) portion $801_1$. Upon contacting an inner surface of the tip shell 905, the irrigant flows towards a distal end 906 via a channel formed between the flex circuit and the inner surface of the conductive tip shell (and flowing around electrode pedestals $831_{1-3}$) before extending radially out of the plurality of irrigation ports/nozzles $902_{1-N}/903_{1-N}$, and/or longitudinally out of distally facing irrigation ports $904_{1-N}$.

Applicant further notes that both the single-piece and two-piece tip insert designs are amenable to use with a flex circuit and/or lead wires, and may be implemented with microelectrodes and/or spot electrodes (e.g., where the flex circuit does not contain metal traces and/or contact pads to implement microelectrodes).

It is further noted that the relative spacing between the first and second portions of the tip insert may vary based on the application-specific irrigant flow characteristics desired. Similarly, the angle of a deflecting surface 893 may also vary as desired (e.g., to achieve desired irrigant dispersement uniformity at a proximal end of the ablation tip).

Many prior art ablation catheter tips include either a rounded tip or a flat-ended tip with a radiused edge. Moreover, these prior art ablation catheter tips are often very smooth, and in some cases even polished. During an ablation therapy, a clinician moves the distal tip of the ablation catheter to various locations within the cardiac muscle where therapy is required. During the therapy, that distal tip of the catheter must remain static (in contact with target tissue) for an extended period of time. If the distal tip accidentally moves during the therapy, the resulting efficacy may be questionable. Many features of the cardiac muscle are known to be difficult to maintain an ablation catheter tip in contact therewith (e.g. the ridge between left pulmonary veins and the left atrial appendage). Moreover, the smooth nature of existing ablation catheter tips may exacerbate a clinician's inability to maintain the ablation catheter tip's position during therapy. Accordingly, aspects of the present disclosure are directed to improving ablation catheter tip stability during ablation therapies. As described in more detail below, stability enhancing features of the ablation catheter tip may be accomplished using laser cut, machine recessed patterns, deep drawn or machine raised patterns, tip surface texturing, and/or spot electrode geometries. FIGS. 4A-7C, and 11A-12B show example embodiments of laser cut patterns that facilitate distributed irrigant flow across the ablation catheter tip and enhance stability when placed in contact with myocardial tissue. In FIGS. 4A-7C, as described in detail above, include laser-cut irrigation ports that run the majority of the ablation catheter tip length, and wrap (at least partially) around the radiused end of the distal tip. The irrigation ports in FIGS. 4A-7C function to improve uniform irrigant distribution and improved tip stability during tip-tissue contact. In more specific reference to FIGS. 11A-C, described in more detail below, additional laser cut features may be added to the tip shell that do not penetrate completely through the tip shell, but serve to facilitate additional catheter tip grip, friction, and/or stability. These additional laser cut features are intended to enhance ablation tip grip when the tip-tissue contact surface experiences a force tangential to the tissue contact surface. In the various embodiments disclosed herein, the additional laser cut features facilitate an enhanced, static frictional coefficient. The alternating chevron rows, for example, may facilitate consistent tip stability regardless of whether the ablation catheter tip is being pushed or pulled across the tissue surface.

Figure 11A:
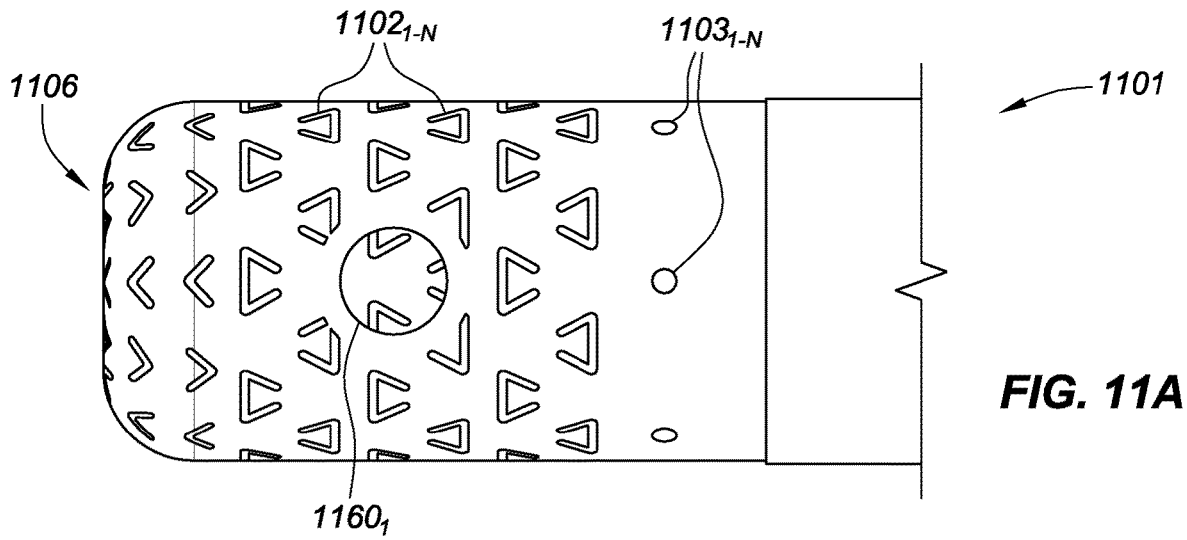
FIG. 11A is a side view of a conductive tip shell of an ablation catheter, consistent with various aspects of the present disclosure.
Figure 11B:
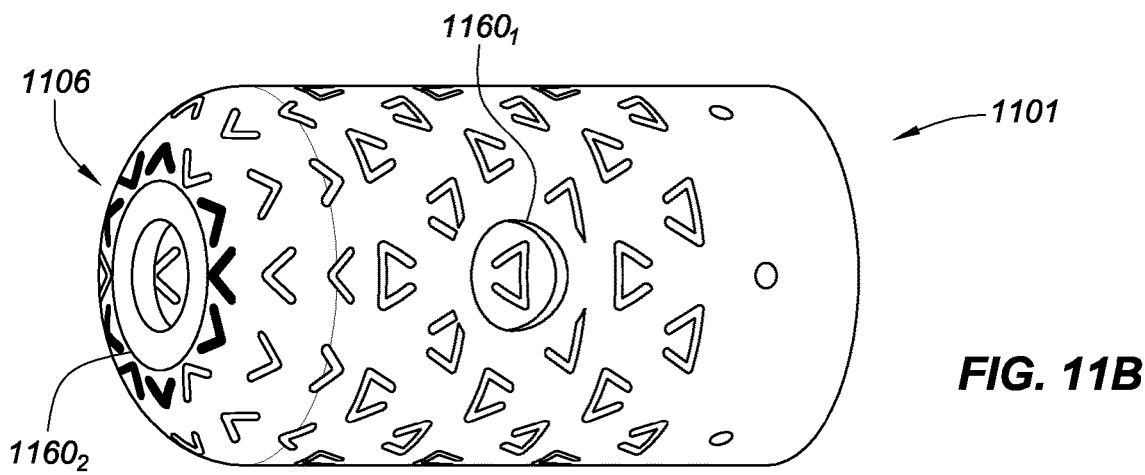
FIG. 11B is a isometric top view of the conductive tip shell of FIG. 11A, consistent with various aspects of the present disclosure.
Figure 11C:
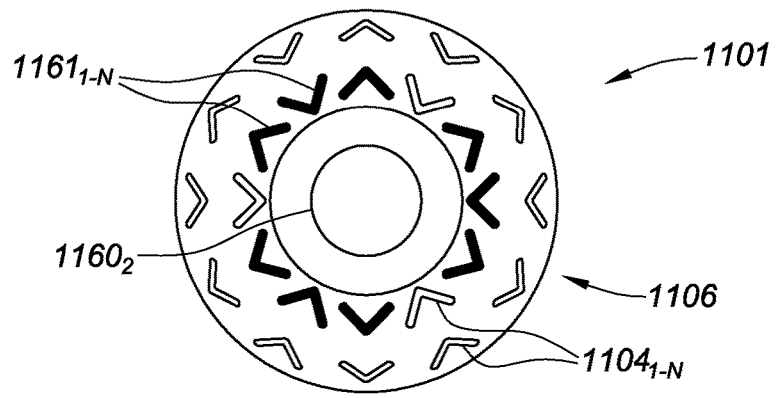
FIG. 11C is a top view of the conductive tip shell of FIG. 11A, consistent with various aspects of the present disclosure.

FIG. 11A is a side view of a conductive tip shell 1101 of an ablation catheter, FIG. 11B is an isometric top view of the conductive tip shell 1101 of FIG. 11A, and FIG. 11C is a top view of the conductive tip shell 1101 of FIG. 11A, consistent with various aspects of the present disclosure. As shown in FIGS. 11A-C, the conductive tip shell 1101 includes cut-outs $1160_{1-3}$ for installation of electrophysiology electrodes which extend (partially) through the conductive tip shell. The conductive tip shell 1101 includes three sets of irrigant ports. A first set of irrigant ports $1103_{1-N}$ is located near a proximal end of the conductive tip shell and comprises a ring of circular ports which extend circumferentially about a diameter of the conductive tip shell. A second set of irrigant ports $1102_{1-N}$ have a partial-triangle shape, are placed in interleaved distally and proximally facing columns, and the rows of the second set of irrigant ports extend circumferentially about an outer diameter of the conductive tip shell. A third set of irrigant ports $1104_{1-N}$ comprise a chevron shape and are positioned in distally facing columns which extend from the outer diameter of the conductive tip shell onto a distal tip 1106. In addition to the third set of irrigant ports which comprise chevrons and which extend through the conductive tip shell 1101, the distal tip 1106 further includes non-irrigating features $1161_{1-N}$. The non-irrigating features, in the present embodiment, do not (necessarily) extend or cut through the conductive tip shell; instead, the non-irrigating features help facilitate enhanced friction between the distal tip 1106 and target tissue for an ablation therapy. As one example, the non-irrigating features $1161_{1-N}$ may be laser cut and have a depth between 0.0005" and 0.005" (but may also be deeper or shallower).

Figure 12A:
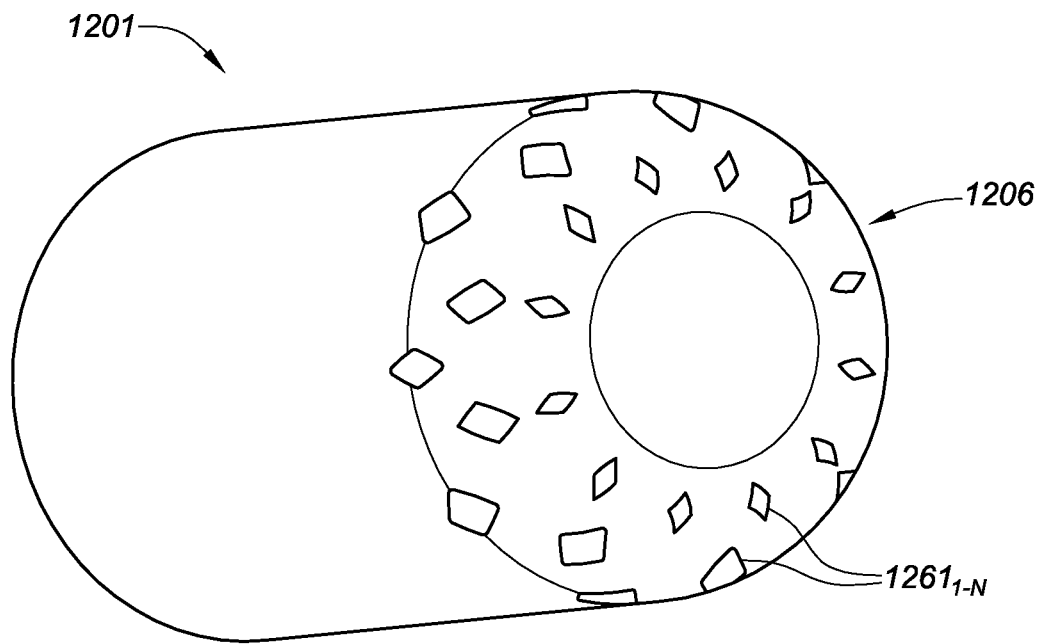
FIG. 12A is an isometric top view of a conductive tip shell of an ablation catheter, consistent with various aspects of the present disclosure.
Figure 12B:
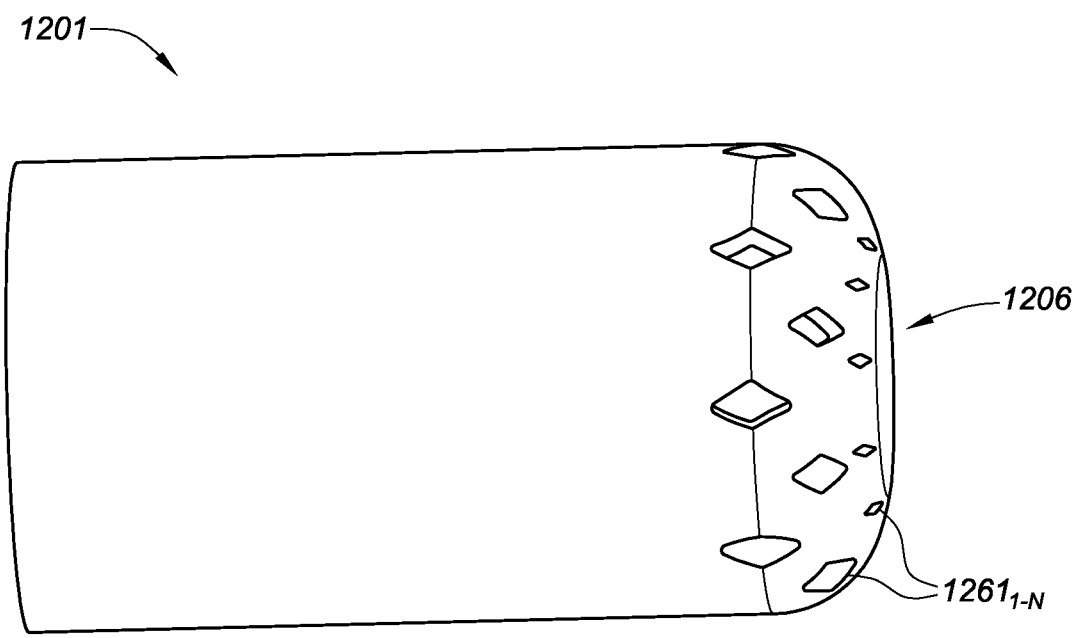
FIG. 12B is a side view of the conductive tip shell of FIG. 12A, consistent with various aspects of the present disclosure.

FIG. 12A is an isometric top view of a conductive tip shell 1201 of an ablation catheter, and FIG. 12B is a side view of the conductive tip shell 1201 of FIG. 12A, consistent with various aspects of the present disclosure. As shown in FIGS. 12A and 12B, a distal tip 1206 of the conductive tip shell includes a plurality of diamond-shaped features $1261_{1-N}$ which may be through-holes to also facilitate irrigation there through, have a blind depth extending partially into the conductive tip shell (or be a combination of both). The diamond-shaped features on the distal tip of the catheter help to facilitate improved tissue grip when the tissue is aligned substantially perpendicular to a longitudinal axis of the catheter shaft.

In the present embodiment, the ablation catheter does not include electrophysiology electrodes for electrophysiology analysis and/or the electrophysiology electrodes are removed for simplifying the discussion of the present embodiment. The various columns of diamond-shaped features may include the same or differently dimensioned diamonds including, for example, different blind depths.

Some or all of the diamond-shaped features may be laser cut to be biased inward or outward from the conductive tip shell outer surface. This biasing would provide for more pronounced edges that would better grip the tissue in contact with the distal tip 1206.

Figure 13A:
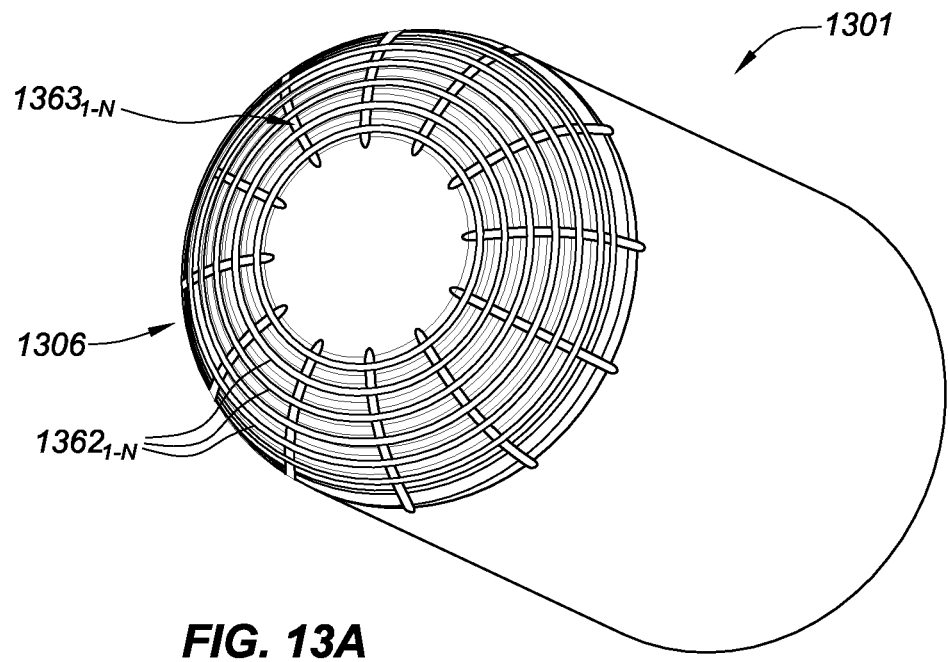
FIG. 13A is an isometric top view of a conductive tip shell of an ablation catheter, consistent with various aspects of the present disclosure.
Figure 13B:
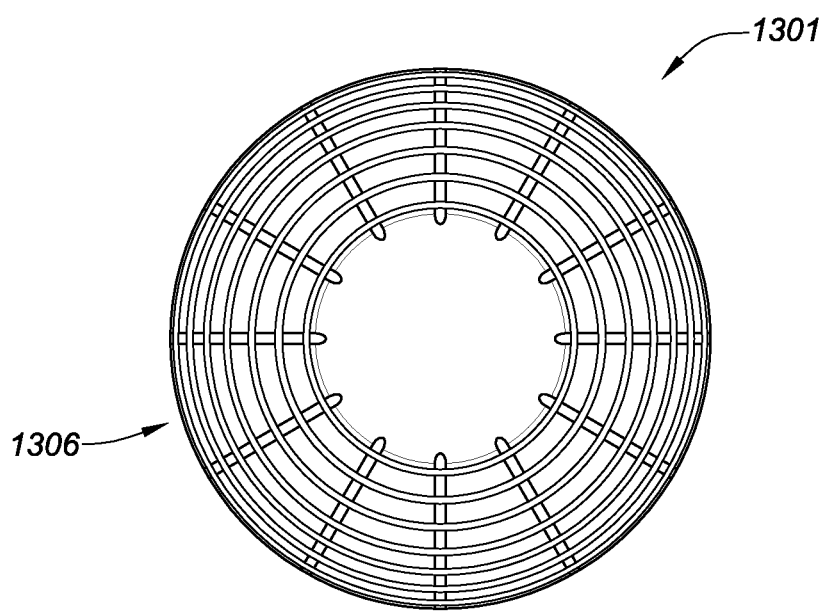
FIG. 13B is a top view of the conductive tip shell of FIG. 13A, consistent with various aspects of the present disclosure.

FIG. 13A is an isometric top view of a conductive tip shell 1301 of an ablation catheter, and FIG. 13B is a top view of the conductive tip shell 1301 of FIG. 13A, consistent with various aspects of the present disclosure. As shown in FIGS. 13A and 13B, a distal end 1306 of the conductive tip shell 1301 includes a plurality of circumferential cuts $1362_{1-N}$ and lateral cuts $1363_{1-N}$ (both of which may or may not extend proximally downward beyond the distal tip on to a tubular portion of the tip shell. In other embodiments, the conductive tip shell may include only circumferential cuts or lateral cuts.

The circumferential and lateral cuts shown in FIGS. 13A and 13B may be proud from the main surface of the tip shell 1301. In some embodiments, to minimize the cost and difficulty of implementation of these features, a deep drawing process may be utilized. A deep drawing process may form the features shown in FIGS. 13A-15B.

Figure 14A:
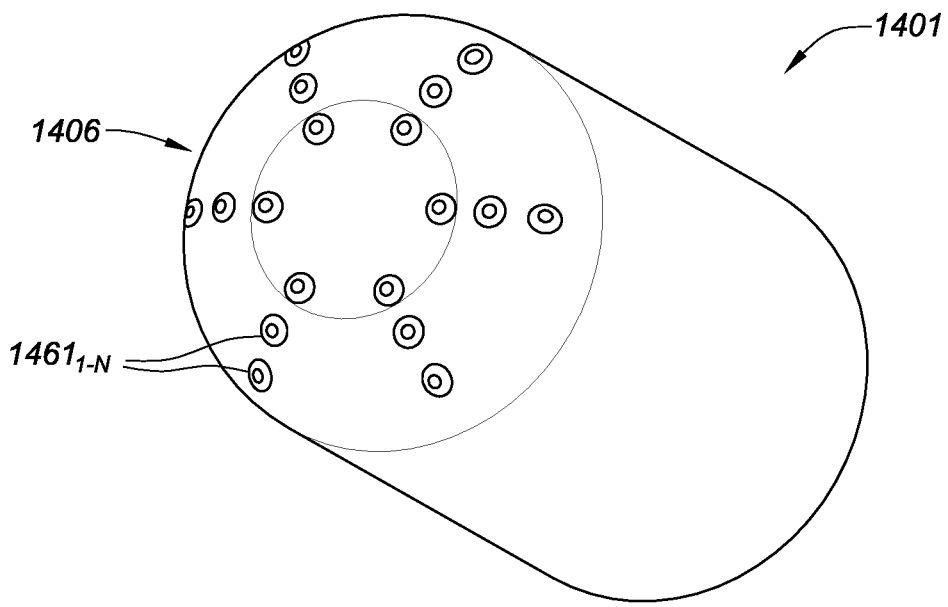
FIG. 14A is an isometric top view of a conductive tip shell of an ablation catheter, consistent with various aspects of the present disclosure.
Figure 14B:
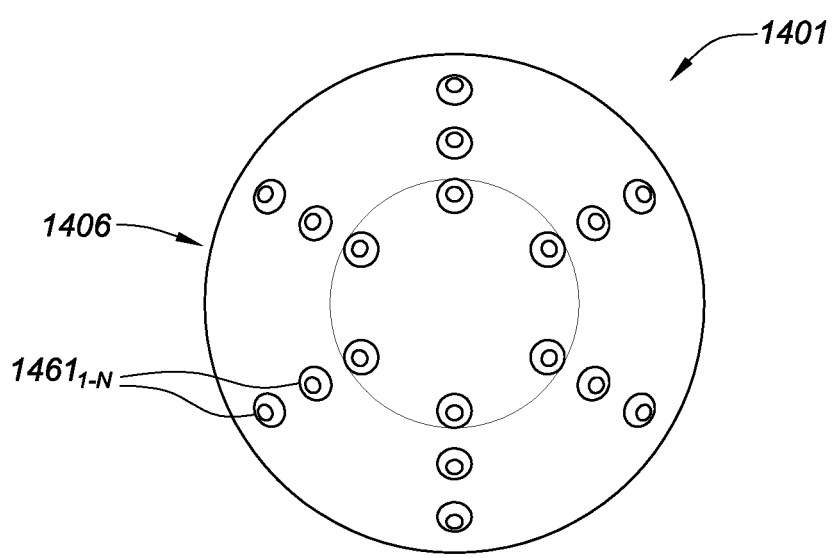
FIG. 14B is a top view of the conductive tip shell of FIG. 14A, consistent with various aspects of the present disclosure.

FIG. 14A is an isometric top view of a conductive tip shell 1401 of an ablation catheter, and FIG. 14B is a top view of the conductive tip shell 1401 of FIG. 14A, consistent with various aspects of the present disclosure. The conductive tip shell 1401, of the present embodiment, includes six columns of circular features $1461_{1-4}$ which are drawn into the outer surface of distal tip 1406 of the tip shell. The six columns are radially distributed about a longitudinal axis of the catheter shaft and extend radially outward and proximally down the length of the tip shell. Each of the columns include three circular features. A skilled artisan will appreciate that various variations on the present embodiment are readily achieved by modifying the number of columns and the number of circular features in each column, as well as the spacing between each of the circular features, the draw depth of the circular features, the diameter of the circular features, etc. Further, these circular features may protrude or otherwise be recessed.

Figure 15A:
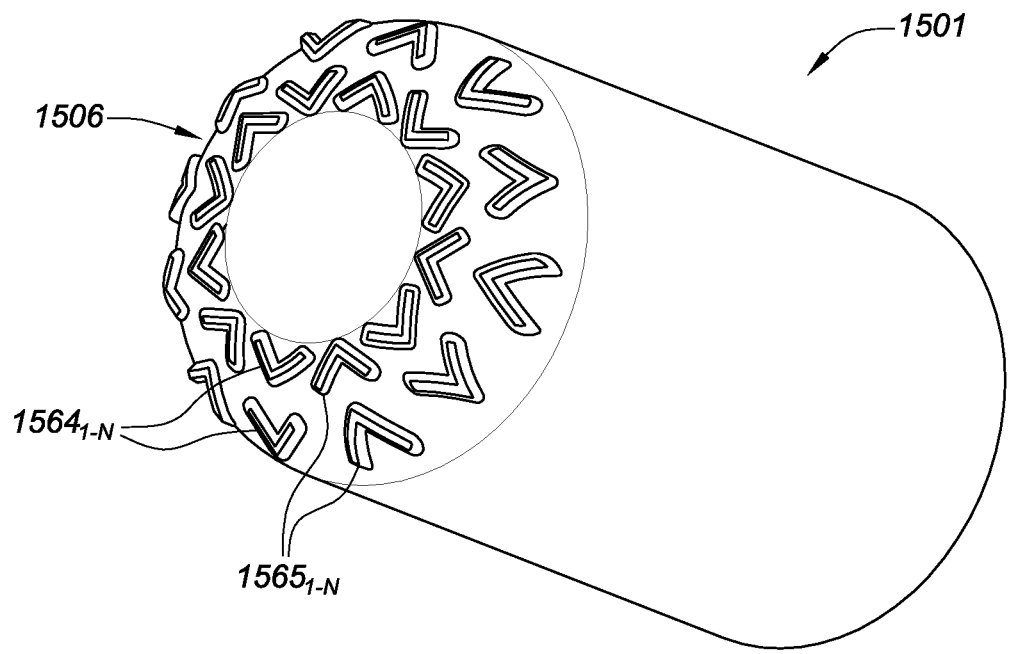
FIG. 15A is an isometric top view of a conductive tip shell of an ablation catheter, consistent with various aspects of the present disclosure.
Figure 15B:
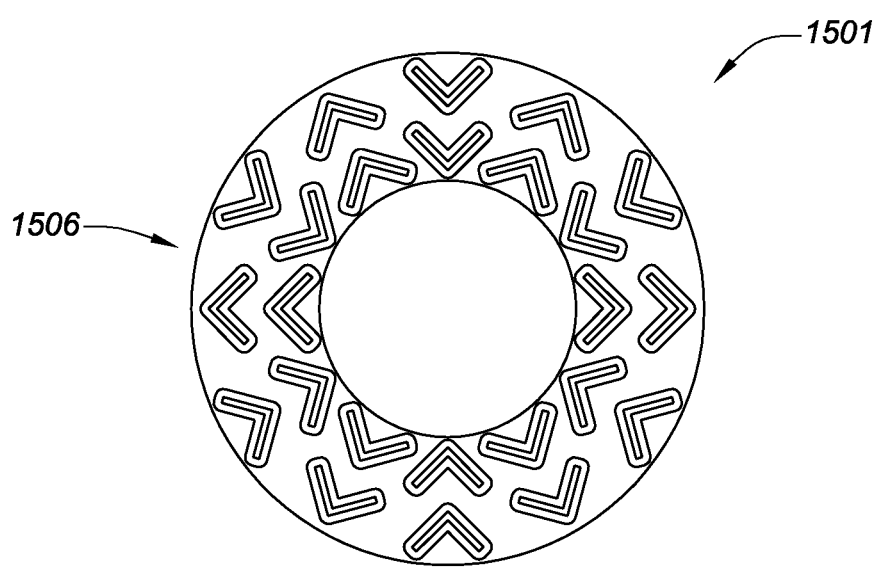
FIG. 15B is a top view of the conductive tip shell of FIG. 15A, consistent with various aspects of the present disclosure.

FIG. 15A is an isometric top view of a conductive tip shell 1501 of an ablation catheter, and FIG. 15B is a top view of the conductive tip shell 1501 of FIG. 15A, consistent with various aspects of the present disclosure. At a distal tip 1506 of the conductive tip shell, a number of inwardly-extending chevrons $1565_{1-N}$, which are positioned in columns relative to one another, are interleaved with outwardly-extending chevrons $1564_{1-N}$, which are also positioned in columns relative to one another. The resulting columns extend inward/outward along a radial path relative to a longitudinal axis of the catheter shaft. As the columns extend about a radius of the distal tip 1506 of the conductive tip shell, the columns begin to extend (at least partially) proximally. Similar to the previous embodiments discussed, these chevrons may be drawn into the outer surface of the tip shell, with some of the displaced material prouding above the outer surface of the distal tip to increase surface area for tip-tissue contact (and the resulting frictional coefficient of the distal tip).

In the various embodiments discussed above, stability enhancing features may include any of the features (irrigating and/or non-irrigating) which are located on a distal surface, crown, and/or hollow shaft of the conductive tip shell.

In various embodiments of the catheter tip assemblies disclosed herein, the catheter tip assemblies may also include a plurality of spot electrodes on a conductive shell thereof which facilitate electrophysiology mapping of tissue, such as myocardial tissue, in (near) contact with the shell. In more specific embodiments, the plurality of spot electrodes may be placed across the shell in such a manner as to facilitate Orientation Independent Algorithms which enhance electrophysiology mapping of the target tissue and is further disclosed in U.S. application Ser. No. 15/152,496, filed 11 May 2016, U.S. application Ser. No. 14/782,134, filed 7 May 2014, U.S. application Ser. No. 15/118,524, filed 25 Feb. 2015, U.S. application Ser. No. 15/118,522, filed 25 Feb. 2015, and U.S. application No. 62/485,875, filed 14 Apr. 2017, all of which are now pending, and are incorporated by reference as though fully disclosed herein.

Optionally, an ablation catheter tip assembly may also include one or more isolated temperature-sensing islands on the conductive shell. The one or more isolated temperature-sensing islands are positioned above thermocouples communicatively coupled to the multi-layer flexible circuit and thermally coupled thereto. Each of these temperature-sensing islands may be outlined or (partially) circumscribed by a strip of insulative material that reduces or eliminates any potential influence from irrigant flowing through nearby irrigation holes in the conductive shell. In particular, if cooled irrigant is flowing through a hole in the conductive shell, heat transfer to the irrigant fluid would meaningfully reduce the temperature of the conductive shell around the hole; however, such heat transfer would not influence a temperature sensor mounted within the conductive shell below the temperature-sensing island.

Catheter tips having a variety of thermometry configurations could be deployed successfully with the pulsed RF control systems described herein. Thus, although the representative catheter tips described herein include, for example six or twelve radially-disposed thermal sensors and one distal thermal sensor placed close to the distal end of the catheter tip, the invention is not limited to such seven-sensor and thirteen-sensor configurations.

Also, catheters comprising various segmented tip designs may work to good advantage with the control systems described above. Some such tip configurations are disclosed in U.S. patent application No. 61/896,304, filed 28 Oct. 2013, and in related international patent application no. PCT/US2014/062562, filed 28 Oct. 2014 and published 7 May 2015 in English as international publication no. WO 2015/065966 A2, both of which are hereby incorporated by reference as though fully set forth herein.

It should also be noted that the control systems (or controller circuitry) described herein may use a "rolling thermocouple," which would, for example, measure the temperature output from each of a plurality of thermocouples every 20 msec (for example) and report the highest of these temperatures to the pulse control box and, potentially, directly to the generator (at least for safety shutdown reasons). In this manner, and in view of the low thermal mass of the ablation tips described herein, the controller is always working with the most accurate representation of the actual tissue temperature. In particular, since the device has low thermal mass, any temperature sensors facing away from the tissue during use of the catheter in an ablation procedure would cool rapidly and their readings could be ignored or discounted, whereas the temperature sensor or sensors closest to the portion of the catheter tip that is in contact with tissue would heat rapidly and would, therefore, provide a temperature reading that is closest to the actual temperature of the tissue being ablated. Thus, by using only the temperature reading from the hottest temperature sensor (or the two or three hottest temperature sensors) at any given time, the system is able to rapidly adjust for the widely varying readings being received from the thermal sensors as the catheter tip is rotated or pushed into tissue during actual use.

Although several embodiments have been described above with a certain degree of particularity, those skilled in the art could make numerous alterations to the disclosed embodiments without departing from the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A high-thermal-sensitivity ablation catheter tip, the tip comprising:
   a conductive shell configured and arranged to conduct ablation therapy;
   a thermally-insulative tip insert positioned such that the conductive shell surrounds at least a portion of the tip insert; and
   a flexible electronic circuit extending around the tip insert, and including
   a plurality of thermal sensors placed in thermal communication with the conductive shell, wherein the plurality of thermal sensors are distributed across at least one of a length and width of the flexible electronic circuit, and
   a plurality of electrodes electrically insulated from the conductive shell and configured to sense electrophysiology characteristics of contacted tissue, wherein the plurality of electrodes are coupled to a distal face of the tip insert and extend through the conductive shell,
   wherein an inner diameter of the conductive shell is less than an outer diameter associated with a circumferential placement of the plurality of electrodes on the distal face of the tip insert, and the inner surface of the conductive shell includes one or more longitudinally extending channels.

2. The high-thermal-sensitivity ablation catheter tip of claim 1, wherein the flexible electronic circuit further includes a wired or wireless communication pathway at least partially disposed on the flexible electronic circuit, communicatively coupled to the plurality of thermal sensors and the plurality of electrodes, and configured to transmit data indicative of the directional temperature feedback and the electrophysiology characteristics of the contacted tissue to an ablation control system.

3. The high-thermal-sensitivity ablation catheter tip of claim 1, wherein the plurality of electrodes are radially offset relative to a longitudinal axis of the catheter tip, and are electrically insulated from the conductive shell by an insulative layer that extends between each of the plurality of electrodes and the conductive shell.

4. The high-thermal-sensitivity ablation catheter tip of claim 1, wherein the plurality of thermal sensors are configured in two circumferential rings around the tip insert, where the first circumferential ring is longitudinally offset relative to the second circumferential ring.

5. The high-thermal-sensitivity ablation catheter tip of claim 4, wherein the plurality of thermal sensors further includes a distal-most thermal sensor placed in thermal communication with a distal tip of the conductive shell.

6. The high-thermal-sensitivity ablation catheter tip of claim 1, wherein the conductive shell further includes an inner surface, and wherein the plurality of thermal sensors are in thermal communication with the inner surface of the conductive shell.

7. The high-thermal-sensitivity ablation catheter tip of claim 1, wherein the tip insert includes a plurality of pedestals positioned on the distal face of the tip insert, the pedestals are configured to position a sensing surface of each of the plurality of electrodes flush with a distal surface of the conductive shell.

8. The high-thermal-sensitivity ablation catheter tip of claim 1, wherein the conductive shell includes a hollow shaft, a distal surface, and a crown which extends between the hollow shaft and the distal surface; and a sensing surface of each of the plurality of electrodes are flush with at least one of the distal surface and the crown of the conductive shell.

9. An ablation tip for an ablation catheter, the ablation tip comprising:
   a thermally and electrically conductive shell that includes an inner surface;
   a thermally-insulative tip insert, wherein the conductive shell surrounds at least a portion of the tip insert; and
   a flexible electronic circuit circumferentially mounted around the tip insert and between the conductive shell and the tip insert, the flexible electronic circuit including
   one or more electrodes electrically insulated from the conductive shell and configured to sense electrophysiology characteristics of contacted tissue, wherein the plurality of electrodes are coupled to a distal face of the tip insert and extend at least partially through the conductive shell,
   wherein an inner diameter of the conductive shell is less than an outer diameter associated with a circumferential placement of the plurality of electrodes on the distal face of the tip insert, and the inner surface of the conductive shell includes one or more longitudinally extending channels.

10. The ablation tip for the ablation catheter of claim 9, wherein the one or more electrodes are electrically insulated from the conductive shell by an insulative layer that extends between each of the electrodes and the conductive shell.

11. The ablation tip for the ablation catheter of claim 9, wherein the flexible electronic circuit further includes
   a plurality of thermal sensors in thermally-transmissive contact with the inner surface of the conductive shell, wherein the plurality of thermal sensors are configured to sense regional temperatures of the conductive shell.

12. The ablation tip for the ablation catheter of claim 11, wherein the flexible electronic circuit further includes
   a wired or wireless communication pathway communicatively connected to the plurality of thermal sensors and the one or more electrodes, and configured to facilitate transmission of data indicative of regional temperatures of the conductive shell and the electrophysiology characteristics of the tissue in contact with the one or more electrodes to an ablation control system.

13. The ablation tip for the ablation catheter of claim 11, wherein the plurality of thermal sensors are configured in two circumferential rings around the tip insert, where the first circumferential ring is longitudinally offset relative to the second circumferential ring.

14. The ablation tip for the ablation catheter of claim 13, wherein the plurality of thermal sensors further includes a distal-most thermal sensor placed in thermal communication with a distal tip of the conductive shell, and the one or more electrodes are circumferentially distributed about the distal-most thermal sensor;
   the conductive shell includes a hollow shaft, a distal surface, and a crown which extends between the hollow shaft and the distal surface; and
   a sensing surface of each of the one or more electrodes are positioned flush with at least one of the distal surface and the crown of the conductive shell.

15. An ablation catheter tip comprising:
   a conductive shell including a distal tip surface, a tubular portion, and a crown extending therebetween; and
   a plurality of electrodes extending through apertures in the crown,
   wherein an inner surface of the conductive shell includes one or more longitudinally extending channels.

16. The ablation catheter tip of claim 15, further including
   a flexible electronic circuit communicatively coupled to the plurality of electrodes; and
   a thermally-insulative ablation tip insert;
   wherein the flexible electronic circuit is wrapped around at least a portion of a circumference of the tip insert; and
   wherein the plurality of electrodes are mounted on a distal surface of the ablation tip insert, and a sensing surface of each of the plurality of electrodes are flush with the crown of the conductive shell.

* * * * *